US008871997B2

(12) United States Patent
Baulcombe et al.

(10) Patent No.: US 8,871,997 B2
(45) Date of Patent: *Oct. 28, 2014

(54) ENHANCED TRANSGENE EXPRESSION BY CO-EXPRESSION WITH A SUPPRESSOR OF POST-TRANSCRIPTIONAL GENE SILENCING (PTGS)

(75) Inventors: David Charles Baulcombe, Norwich (GB); Olivier Voinnet, Zürich (CH); Andrew John Hamilton, Helensburgh (GB)

(73) Assignee: Plant Bioscience Limited, Norwich (GB)

( * ) Notice: Subject to any disclaimer, the term of this patent is extended or adjusted under 35 U.S.C. 154(b) by 1677 days.

This patent is subject to a terminal disclaimer.

(21) Appl. No.: 11/602,416

(22) Filed: Nov. 20, 2006

(65) Prior Publication Data
US 2007/0292862 A1 Dec. 20, 2007

Related U.S. Application Data

(63) Continuation of application No. 10/130,758, filed as application No. PCT/GB00/04454 on Nov. 22, 2000, now Pat. No. 7,217,854.

(30) Foreign Application Priority Data

Nov. 22, 1999 (GB) .................................. 9927609.9
Sep. 19, 2000 (GB) .................................. 0022960.9
Sep. 27, 2000 (GB) .................................. 0023668.7

(51) Int. Cl.
| C12N 15/33 | (2006.01) |
| C12N 15/69 | (2006.01) |
| C12N 15/82 | (2006.01) |
| C12N 15/87 | (2006.01) |
| C12N 9/12 | (2006.01) |

(52) U.S. Cl.
CPC .......... *C12N 9/1205* (2013.01); *C12N 15/8257* (2013.01); *C12N 15/8218* (2013.01); *C12N 15/8203* (2013.01)
USPC .......... 800/278; 435/71.1; 435/468; 435/469; 435/419

(58) Field of Classification Search
None
See application file for complete search history.

(56) References Cited

U.S. PATENT DOCUMENTS

| 5,939,541 A | 8/1999 | Vance |
| 7,267,985 B2 * | 9/2007 | Vance ........................ 435/468 |
| 2005/0022262 A1 | 1/2005 | Vance |

FOREIGN PATENT DOCUMENTS

| WO | 98/44097 | 10/1998 |
| WO | 01/34822 | 5/2001 |

OTHER PUBLICATIONS

Scholthof et al., Plant Virus Gene Vectors for Transient Expression of Foreign Genes in Plants, Annu. Rev. Phytopathol. 1996, vol. 34, pp. 299-323.*
Voinnet et al., An enhanced transient expression system in plants based on suppression of gene silencing by the p19 protein of tomato bushy stunt virus, Plant J., 2003, vol. 33, pp. 949-956.*
Hanley-Bowdin et al., Transient expression of heterologous RNAs using tomato golden mosaic virus, Nucl. Acids Res., 1988, vol. 16, pp. 10511-10528.*
Turpen et al. (1993) J. of Virological Methods 42: 227-239.*
Kubota et al., J. Virol., 2003, vol. 77, pp. 11016-11026.
Gonzalez-Jara et al., Phytopath., 2005, vol. 95, pp. 894-901.
Anandalakshmi et al., Science, 2000, vol. 290, pp. 142-144.
Angell et al., Embo J., vol. 16, pp. 3675-3684, (1997).
Vazquez-Tello et al., Mol. Gen. Genet., 1998, vol. 257, pp. 157-166.
Angell et al., Virol., 1995, vol. 215, pp. 197-201.
Pruss, G. et al. "Plant Viral Synergism: The Potyviral Genome Encodes a Broad-Range Pathogenicity Enhancer That Transactivates Replication of Heterologous Viruses"; The Plant Cell, 9: 859-868 (1997).
Anandalakshmi, R. et al. "A viral suppressor of gene silencing in plants"; Proc. Natl. Acad. Sci. USA, 95:13079-13084 (1998).
Brigneti, G. et al. "Viral pathogenicity determinants are suppressors of transgene silencing in *Nicotiana benthamiana*"; The EMBO Journal, 17(22): 6739-6746 (1998).
Kasschau, K.D. et al. "A counterdefensive Strategy of Plant Viruses: Suppression of Posttranscriptional Gene Silencing"; Cell, 95: 461-470 (1998).
Beclin, C. et al. "Infection of Tobacco or *Arabidopsis* Plants by CMV Counteracts Systemic Post-transcriptional Silencing of Nonviral (Trans)Genes"; Virology, 252:313-317 (1998).

(Continued)

*Primary Examiner* — Anne Kubelik
*Assistant Examiner* — Steven Bernacki
(74) *Attorney, Agent, or Firm* — Dann, Dorfman, Herrell & Skillman; Kathleen D. Rigaut; Robert C. Netter, Jr.

(57) ABSTRACT

Disclosed are a variety of methods for achieving enhanced expression from a target nucleotide sequence in a plant e.g. comprising the step of transiently introducing into a tissue of a plant (e.g. a leaf) a first nucleic acid comprising the target nucleotide sequence and a second nucleic acid encoding a Post Transcriptional Gene Silencing (PTGS) suppressor protein (preferably of viral or plant origin), wherein the first and second nucleic acids are comprised within a single binary vector, construct, or the first and second nucleic acid sequences are comprised within a first binary vector and a second binary vector construct respectively. The plant tissue may then be harvested for the protein. Such methods can give much higher levels of gene expression than are obtainable using stable transgenes, or certain replicating vectors. Also disclosed are specific PTGS suppressor proteins: potato virus X (pvx), p25 protein; african cassava mosaic virus (acmv) AC2 protein; rice yellow mottle virus (rymv) P1 protein; tomato bushy stunt virus (tbsv) 19K protein; plus variants of these. These suppressors may be used in any PTRS context, including the enhancement of transient expression systems.

19 Claims, 4 Drawing Sheets

(56) References Cited

OTHER PUBLICATIONS

Vionnet, O. et al. "Suppression of gene silencing: A general strategy used by diverse DNA and RNA viruses of plants"; Proc. Natl. Acad. Sci. USA, 96(24): 14147-14152 (1999).

Bonneau, C., et al., "Expression of the rice yellow mottle virus P1 protein in vitro and in vivo and its involvement in virus spread," Virology, 244(1):79-86 (Apr. 25, 1998).

Saunders, K., et al., "Complementation of African cassava mosaic virus AC2 gene function in a mixed bipartite geminivirus infection," J. General Virology, 76(9):2287-2292 (1995).

Hong, Y., et al., "Transactivation of dianthin transgene expression by African cassava mosaic virus AC2," Virology 228(2):383-387 (Feb. 17, 1997).

Scholthof, H.B., et al., "Identification of tomato bushy stunt virus host-specific symptom determinants by expression of individual genes from a potato virus X vector," Plant Cell 7(8):1157-1172 (1995).

Voinnet, O., et al., "A viral movement protein prevents spread of the gene silencing signal in *Nicotiana benthamiana*," Cell 103(1):157-167 (Sep. 29, 2000).

\* cited by examiner

Figure 1:
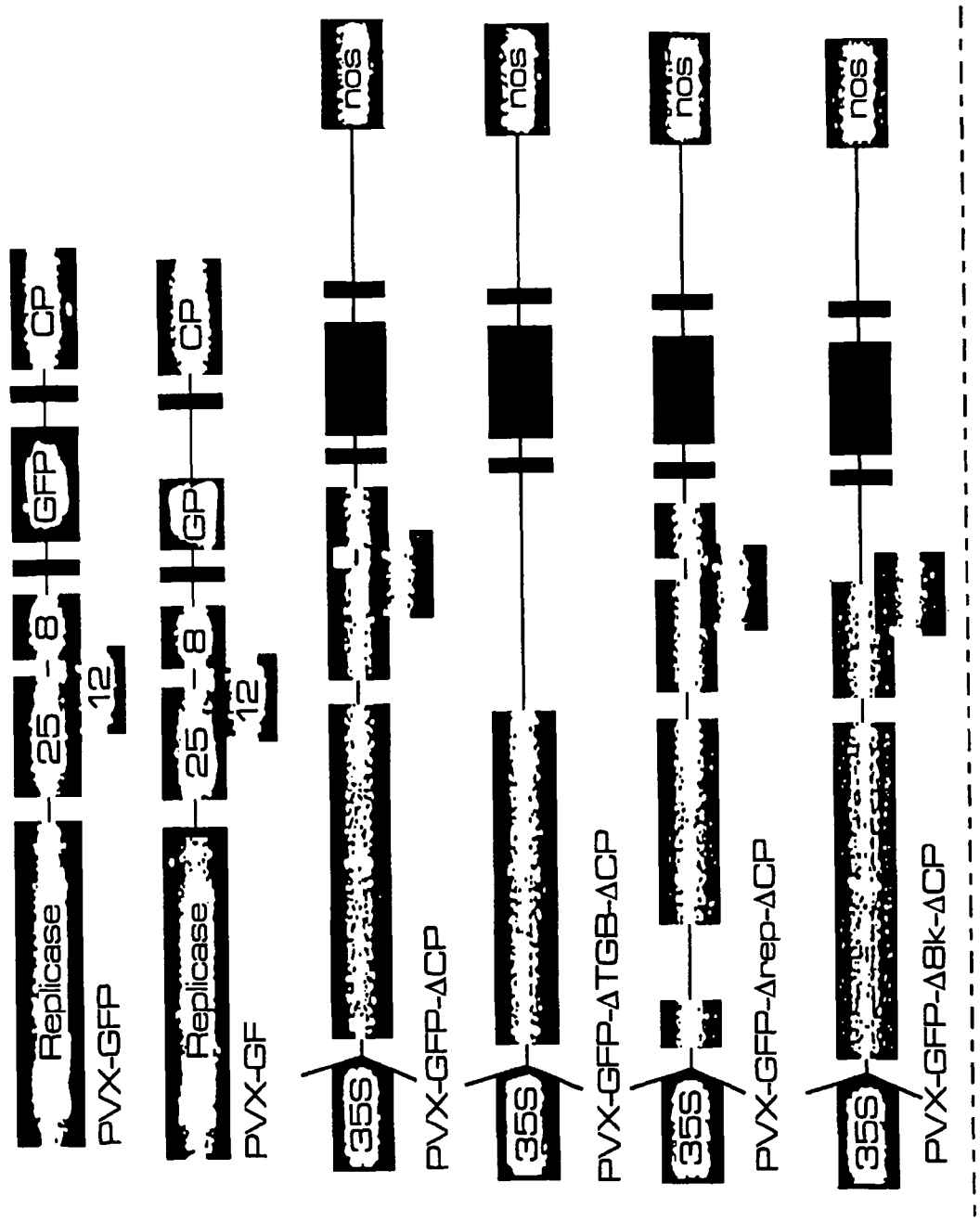

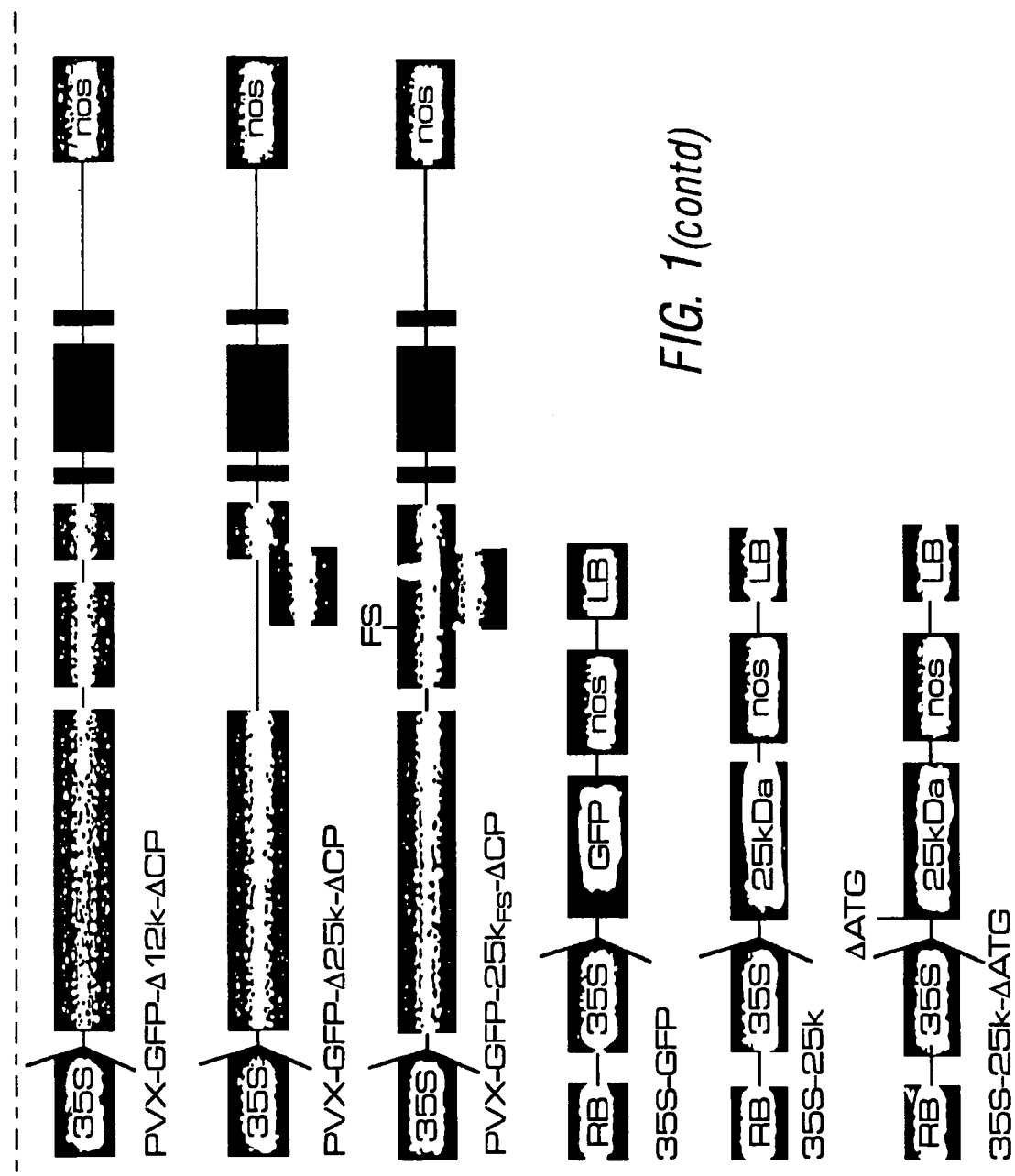
FIG. 1 (contd)

ENHANCED TRANSGENE EXPRESSION BY CO-EXPRESSION WITH A SUPPRESSOR OF POST-TRANSCRIPTIONAL GENE SILENCING (PTGS)

PRIORITY

This application is a continuation application of U.S. patent application Ser. No. 10/130,758 filed Oct. 8 2002, now U.S. Pat No. 7,217,854 which is a §371 Application of PCT/GB00/04454 filed 22 Nov. 2000, which in turn claims priority to GB applications 9927609.9 filed 22 Nov. 1999, 0022960.9 filed 19 Sep. 2000 and 0023668.7 filed 27 Sep. 2000. The foregoing applications are incorporated by reference herein.

TECHNICAL FIELD

The present invention relates generally to methods and materials for use in suppressing gene silencing, particularly post-transcriptional gene silencing, and for boosting gene expression.

PRIOR ART

In plants, post-transcriptional gene silencing (PTGS) is manifested as the reduction in steady-state levels of specific RNAs after introduction of homologous sequences in the plant genome. This reduction is caused by an increased turn-over of target RNA species, with the transcription level of the corresponding genes remaining unaffected (reviewed in (1)).

PTGS can be initiated in a variety of ways, and is thought to underlie the phenomena of co-suppression of endogenous plant genes, and depressed expression of transgenes. In transformed plants, PTGS is targeted against transcripts of the transgene and any similar endogenous genes so that the corresponding gene products accumulate at a low level (Vaucheret et al., 1998).

One of the most intriguing features of PTGS in transgenic plants is that it is not cell autonomous. A signal of gene silencing can move between cells through plasmodesmata and long distances through the vascular system, directing sequence-specific degradation of target RNAs (2, 3). The nature of the signal is not known but, based on the specificity of its action, it is thought to incorporate a nucleic acid. The specificity of the degradation mechanism may be mediated by short RNA species corresponding to the target RNA that accumulate in tissues exhibiting PTGS (Hamilton and Baulcombe, 1999—described therein as being 25 nucleotides, though may be 21-23 nucleotide (nt) RNA).

Although the exact mechanism by which PTGS operates is yet to be elucidated, various findings that viruses can both initiate and be a target of PTGS (4) led to the suggestion that PTGS is a natural mechanism by which plants recognise and combat foreign nucleic acids (5). In support of the proposed relationship between PTGS and virus resistance, it was shown that some viruses induce an RNA-mediated defense (RMD) in non-transgenic plants. This induced defense is similar to PTGS in that it is characterised by nucleotide sequence-specific resistance against virus infection (6). In infected cells, PTGS is targeted against the viral RNA and causes its accumulation or slow down or stop at late stages in the infection process (Ratcliff et al., 1999). In some, but not all instances, the upper leaves of plants exhibiting this RMD are said to have recovered because they contain only low levels of viral RNA and are symptom-free (7, 8).

The role of PTGS in virus protection is illustrated by the phenotype of sgs2 mutant Arabidopsis plants infected with cucumber mosaic virus (CMV) (Mourrain et al., 2000). These plants are defective in PTGS and hyper-susceptible to the virus. In addition, with caulimo-, nepo-, potex-and tobraviruses there is evidence that PTGS accounts, at least in part, for cross protection against infection with a second virus (Covey et al., 1997; Ratcliff et al., 1997; Ratcliff et al., 1999). The first virus induces PTGS so that the infected cells are primed to resist the second virus in a nucleotide-specific manner. Silencing of endogenous genes in plants infected with tobamo-, potex and gemini-virus vectors carrying elements of host sequences is also an indication that PTGS is an antiviral defense mechanism (Baulcombe, 1999). Following the onset of virus replication, PTGS is targeted against sequences in the viral genome and expression of the corresponding endogenous genes is suppressed.

The discovery that PTGS is transported systemically in transgenic plants has prompted speculation that it also operates in a non-cell autonomous manner during natural virus infections (Voinnet et al., 1998; Jorgensen et al., 1998; Carrington, 1999; Lucas and Wolf, 1999). A virus-induced silencing signal could migrate cell-to-cell in advance of the infection front and be transported over long distances through the phloem. The effect of this intercellular signalling would be to potentiate RNA sequence-specific virus resistance in non-infected tissues and, consequently, to delay spread of the virus through the plant.

Notwithstanding the above, the ability of viruses to infect plants indicates that they have evolved to avoid or suppress the RMD.

This idea was first prompted by analysis of potyviral synergistic interactions with other viruses (9). It was shown that this synergism was due to suppression of a host defense mechanism by the Hc-protease (HcPro) encoded in the potyviral genome (10), examples including tobacco vein mottling virus (TVMV); tobacco etch virus (TEV) and potato virus Y (PVY). Subsequent studies further established that HcPro was a suppressor of PTGS and provided a link between PTGS and antiviral defense (11-13). Presumably, the suppression acts against the RMD evoked above.

A second protein, the 2b protein of cucumber mosaic virus (CMV), was also identified as a suppressor of PTGS in *N. benthamiana* (12). The proteins 2b and HcPro are dissimilar at the protein sequence level, and interestingly they do not target the silencing mechanism in the same way: HcPro suppresses silencing in tissues where it was already established, whereas the 2b protein only affects silencing initiation (12, 14).

Suppressors of gene silencing can be used inter alia for improving expression of desirable genes, particularly heterologous genes, in plants (see WO 98/44097 of Vance et al). In addition, the increasing body of evidence that PTGS also operates in animals raises the possibility that silencing suppression has also been adopted by animal viruses (31) and such suppressors may be of relevance to gene expression in e.g. mammals.

Thus it can be seen that the identification of suppressors of gene silencing, or sources thereof, would provide a contribution to the art.

DISCLOSURE OF THE INVENTION

A number of suppressors of gene silencing from a variety of viruses have been identified. The ability to suppress PTGS was assessed by infecting *N. benthamiana* plants exhibiting PTGS of a GFP transgene with the viruses, or with PVX vectors expressing particular viral pathogenicity determinants.

Suppressors such as those disclosed herein may be used, inter alia, to suppress silencing in those instances where it is not desired.

Separate experiments employed a novel PVX-based-experimental system in which movement of a virus-induced signal could be uncoupled from movement of the virus. This demonstrated that an antiviral signal molecule could be transported over several centimetres from the infected cells to accumulate in and around the veins of recipient leaves. However the 25kDa protein of PVX (p25) suppresses the systemic PTGS response. In earlier models, the p25 protein of PVX had been characterized as a movement protein and was considered as a facilitator of channel gating (Angell et al., 1996). The work described below suggests a further facilitating role for it.

Further experiments with p25 demonstrated two branches in the PTGS pathway. One branch appears to be activated by replicating viral RNA and is not affected by p25. The second branch can be activated by non replicating RNA of viral or transgene origin and is suppressed by p25. The systemic signal appears to be produced in the second, p25-sensitive branch of the pathway, and is likely to be a precursor of short RNA species of 21-23 nucleotides or so. Amongst other things, these observations demonstrate that p25 may be used to specifically inhibit systemic silencing of a target gene (i.e. enhance, relatively, its expression). It may be used to preferentially enhance expression (impair suppression) of a target transgene in a plant, without equivalent impairment of the suppression of virally-expressed genes (which could increase the susceptibility of the plant to viral diseases).

In a further aspect of the invention, a variety of suppressors (both novel suppressors, and those of the prior art) have been used in conjunction with a 'transient' expression system to generate very high, levels of the protein over a sustained expression period (generally a matter of days). Particular experiments employed transient expression of a suppressor in conjunction with transient expression of a desired protein, in each case from a plant binary vector. The results were particularly surprising, not only because of the highly (i) enhanced, and (ii) sustained, expression levels which were achieved, but also because it was hitherto unknown that PTGS played any role in the 'transient' nature of the expression which results from constructs used in this way. Indeed, the results herein show that when used in the presence of suppressors, the term 'transient' is in one respect a misnomer, since in some cases expression is sustained as long as the cells remain viable. Nevertheless, the term 'transient' will be used for convenience, and since those skilled in the art will be familiar with it. In preferred aspects of the invention, this system can be used as a rapid method to generate protein in a plant or part thereof, at higher levels, and more conveniently, than by use of 'stable' (integrated) transgenes, or viral vectors. Alternatively it can be used as a sensitive 'trap' assay for identifying putative suppressors. Putative suppressors may derive from any source e.g. plants, animals or viruses.

With reference to the various aspects of the invention, and viruses discussed below, the following abbreviations are used:
tobacco vein mottling virus (TVMV);
tobacco etch virus (TEV) [a potyvirus];
potato virus Y (PVY) [a potyvirus];
cucumber mosaic virus (CMV)[a cucumovirus];
tobacco mosaic virus (TMV) [a tobamovirus];
potato virus X (PVX) (a potexvirus);
tomato bushy stunt virus (TBSV) [a tombusvirus];
rice yellow mottle virus (RYMV) [a sobemovirus];
african cassava mosaic virus (ACMV) [a geminivirus];
narcissus mosaic virus (NMV) [a potexvirus];
nandina virus X (NVX) [a potexvirus];
viola mosaic virus (VMV) [a potexvirus],
cowpea mosaic virus (CPMV) [a comovirus];
foxtail mosaic virus (FOMV) [a potexvirus];
alfalfa mosaic virus (AMV);
tobacco black ring virus (TBRV) [a nepovirus];

Those wild type and recombinant viruses which produced suppressors of a PTGS-like resistance mechanism, which interfered with PTGS of the GFP, include TMV; TBSV; RYMV; ACMV; NMV; NVX; VMV and CPMV.

In the first PTGS suppression assay described in the Examples below, the relevant viruses produced a characteristic pattern of silencing suppression. Some, like potyviruses, suppressed in young and old leaves. Others were like CMV and affected only young leaves. There was also variation in the tissue specificity with ACMV, NMV, NVX, VMV, and PVX-P1 affecting all tissues whereas TBSV, TMV and CPMV specifically suppressed silencing in tissues that were in or close to the veins. This phenotype of silencing suppression that operates in the vicinity of the veins was previously uncharacterised. Interestingly, although TMV, TBSV and CPMV are only able to suppress PTGS in or near the veins, they are nevertheless able to accumulate at a high level throughout the infected leaf. It is therefore clear that suppression of PTGS is by no means the only strategy adopted by viruses for enhancing pathogenicity and counteracting the effects of RMD.

In the second (systemic) PTGS suppression assay, based on grafting experiments and\or movement defective forms of PVX, systemic signaling of PTGS was only observed for PVX when the 25kDa viral movement protein (p25) was modified or removed.

In addition to the novel role for p25, at least three novel viral protein suppressors of PTGS have been specifically isolated (the ACMV AC2, the RYMV P1 and the TBSV 19K proteins). These viruses are not closely related to the potyviruses discussed above. ACMV is a DNA geminivirus (26, 27). RYMV is a sobemovirus, TBSV is a tombusvirus.

Interestingly the viral suppressors of gene silencing appear to be quite diverse, and no common structural features in these proteins have been identified. It thus appears that the suppressor function has evolved independently several times as a strategy to counteract the effects of RMD.

Particular aspects of the invention will now be discussed in more detail.

Definitions

The term "heterologous" is used broadly below to indicate that the gene/sequence of nucleotides in question have been introduced into the cells in question (e.g. of a plant or an ancestor thereof) using genetic engineering, i.e. by human intervention. A heterologous gene may replace an endogenous equivalent gene, i.e. one which normally performs the same or a similar function, or the inserted sequence may be additional to the endogenous gene or other sequence. Nucleic acid heterologous to a cell may be non-naturally occurring in cells of that type, variety or species. Thus the heterologous nucleic acid may comprise a coding sequence of, or derived from, a particular type of plant cell or species or variety of plant, placed within the context of a plant cell of a different type or species or variety of plant. A further possibility is for a nucleic acid sequence to be placed within a cell in which it or a homologue is found naturally, but wherein the nucleic acid sequence is linked and/or adjacent to nucleic acid which does not occur naturally within the cell, or cells of that type or species or variety of plant, such as operably linked to one or more regulatory sequences, such as a promoter sequence, for control of expression. "Gene" unless context demands otherwise refers to any nucleic acid encoding genetic information for translation into a peptide, polypeptide or protein.

"Vector" is defined to include, inter alia, any plasmid, cosmid, phage, viral or Agrobacterium binary vector in double or single stranded linear or circular form which may or may not be self transmissible or mobilizable, and which can transform a prokaryotic or eukaryotic host either by integration into the cellular genome or exist extrachromosomally (e.g. autonomous replicating plasmid with an origin of replication). Specifically included are shuttle vectors by which is meant a DNA vehicle capable, naturally or by design, of replication in two different host organisms, which may be selected from actinomycetes and related species, bacteria and eucaryotic (e.g. higher plant, mammalian, yeast or fungal cells). A vector according to the present invention need not include a promoter or other regulatory sequence, particularly if the vector is to be used to introduce the nucleic acid into cells for recombination into the genome.

"Expression vector" refers to a vector in which a nucleic acid is under the control of, and operably linked to, an appropriate promoter or other regulatory elements for transcription in a host cell such as a microbial or plant cell. The vector may be a bi-functional expression vector which functions in multiple hosts. In the case of genomic or subgenomic DNA, this may contain its own promoter or other regulatory elements and in the case of cDNA this may be under the control of an appropriate promoter or other regulatory elements for expression in the host cell A "promoter" is a sequence of nucleotides from which transcription may be initiated of DNA operably linked downstream (i.e. in the 3' direction on the sense strand of double-stranded DNA).

"Operably linked" means joined as part of the same nucleic acid molecule, suitably positioned and oriented for transcription to be initiated from the promoter.

The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus.

Use of Suppressors

In a first aspect of the present invention there is disclosed use of a gene silencing suppressor protein obtainable from a virus may be selected from: PVX; TMV; TBSV; RYMV; ACMV; NMV; NVX; VMV and CPMV.

The term 'suppress' in this context does not imply a requirement that PTGS be totally negated. The suppression may be partial, for instance in terms of localisation (e.g. restricted to in and around leaf veins) temporally (e.g. inhibits the initiation of PTGS, rather than existing silencing) or intensity (i.e. PTGS continues at a reduced level). The term is used herein where convenient because those skilled in the art well understand this.

The suppression may also be with respect of the systemic signal of PTGS, which is to say that the spread of PTGS can be inhibited. This may be achieved using p25 or a variant thereof.

Preferably the suppressor is selected from: the ACMV AC2 protein; PVX p25 protein; the RYMV P1 protein; or the TBSV 19K protein, or variants thereof. Preferably it is the 19K or p25 protein, or a variant of either. Most preferably it is the 19K protein, or a variant thereof.

The P1 protein in particular has been found to operate in both monocot and dicot plants. This is surprising because P1 is associated with a virus which only affects monocots (e.g. wheat, rice and barley). This versatility of P1 makes it particular suitable for enhancing expression in a wide variety of plant types.

The sequences of the p25, AC2; P1 and 19K proteins are disclosed as follows:

p25 sequence is described by Huisman et al (1988) J Gen Virol, Vol. 69 pp 1789-1798.

The AC2 sequence is described by Stanley J (1983) Nature, vol. 361 No 5897 pp 260-262.

The P1 sequence is described by Bonneau C et al (1998) Virology 244, pp 79-86.

The 19K sequence is described by Scholtoft H et al (1995) Plant Cell 7, pp 1157-1172.

All of these sequences are specifically incorporated herein by reference.

Where suppressors are used herein e.g. within nucleic acid constructs, the constructs may be free or substantially free of other sequences or proteins associated with the suppressor in nature (e.g. viral proteins, if the suppressor is derived from a virus).

The invention also embraces use of a variant of any of these sequences. A variant protein shares homology with, or is identical to, all or part of the sequences discussed above and will be capable of suppressing PTGS, which activity can be confirmed using the methods disclosed or otherwise referred to herein. Such methods may comprise the step of comparing the PTGS-suppressing effect of the native or reference protein, with that of the variant, and with a control (such as the 'm' controls discussed in the Examples).

Generally speaking, wherever the term is used herein, variants may be:

(i) naturally occurring homologous variants of the relevant suppressor, for instance as obtainable from different viral strains or isolates to those used above, or may be isolated in future from related viruses. Where used with respect to suppressors from plants or animals, it likewise include alleles, paralogues, orthologues etc.

(ii) artificially generated homologous variants (derivatives) which can be prepared by the skilled person in the light of the present disclosure, for instance by site directed or random mutagenesis, or by direct synthesis. Preferably the variant nucleic acid, encoding the variant polypeptide, is generated either directly or indirectly (e.g. via one or more amplification or replication steps) from an original nucleic acid encoding one of the suppressors discussed above. Changes to the nucleic acid sequence may produce a derivative by way of one or more of addition, insertion, deletion or substitution of one or more nucleotides in the nucleic acid, leading to the addition, insertion, deletion or substitution of one or more amino acids in the encoded polypeptide. Desirable mutation may be random or site directed mutagenesis in order to alter the activity (e.g. specificity) or stability of the encoded polypeptide. Changes may be by way of conservative variation, i.e. substitution of one hydrophobic-residue such as isoleucine, valine, leucine or methionine for another, or the substitution of one polar residue for another, such as arginine for lysine, glutamic for aspartic acid, or glutamine for asparagine. Also included are variants having non-conservative substitutions. In regions which are critical in determining the peptides conformation or activity such changes may confer advantageous properties on the polypeptide e.g. altered stability or specificity. Particularly included are fragments of the suppressors which maintain PTGS-suppressing activity.

Similarity or homology in the case of variants is preferably established via sequence comparisons made using FASTA and FASTP (see Pearson & Lipman, 1988. Methods in Enzymology 183: 63-98). Parameters are preferably set, using the default matrix, as follows:

Gapopen (penalty for the first residue in a gap): −12 for proteins/−16 for DNA

Gapext (penalty for additional residues in a gap): −2 for proteins/−4 for DNA

KTUP word length: 2 for proteins/6 for DNA.

Homology may be at the nucleotide sequence and/or encoded amino acid sequence level. Preferably, the nucleic acid and/or amino acid sequence shares at least about 75%, or 80% identity, most preferably at least about 90%, 95%, 96%, 97%, 98% or 99% identity.

Homology may also be assessed by use of a probing methodology (Sambrook et al., 1989). One common formula for calculating the stringency conditions required to achieve hybridization between nucleic acid molecules of a specified sequence homology is: $T_m=81.5°$ C.+16.6 Log[Na+]+0.41 (% G+C)−0.63 (% formamide)−600/#bp in duplex. As an illustration of the above formula, using [Na+]=[0.368] and 50-% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

Thus this aspect of the invention particularly embraces use of the p25, AC2, P1 or 19K protein, or homologues or derivatives of any of these.

Generally speaking, and as described in more detail below, the suppressor may be employed in the methods of the present invention by infection from a progenitor virus, or by expression from an appropriate nucleic acid construct (based e.g. on cDNA, RNA, genomic DNA etc.). Where a DNA sequence is specified, unless context requires otherwise, use of the RNA equivalent, with U substituted for T where it occurs, is encompassed. Nucleic acid encoding suppressors according to the present invention may be utilised in isolated and/or purified form e.g. free or substantially free of nucleic acid comprising other nucleotide sequences of the viral strain of origin. The nucleic acid molecules used may be wholly or partially synthetic. In particular they may be recombinant in that nucleic acid sequences which are not found together in nature (do not run contiguously) have been ligated or otherwise combined artificially e.g. suppressors and heterologous sequences which it is desired to express.

Use in Plants

As described below, in its various aspects, the invention will generally be employed in plants, using nucleic acids encoding suppressors identified for the first by the present inventors, or in certain cases those of the prior art.

Specific procedures and vectors previously used with wide success upon plants are described by Guerineau and Mullineaux (1993) (Plant transformation and expression vectors. In: Plant Molecular Biology Labfax (Croy RRD ed) Oxford, BIOS Scientific Publishers, pp 121-148). Suitable vectors may include plant viral-derived vectors (see e.g. EP-A-194809).

Suitable promoters which operate in plants include the Cauliflower Mosaic Virus 35S (CaMV 35S). Other examples are disclosed at pg 120 of Lindsey & Jones (1989) "Plant Biotechnology in Agriculture" Pub. OU Press, Milton Keynes, UK. The promoter may be selected to include one or more sequence motifs or elements conferring developmental and/or tissue-specific regulatory control of expression. Inducible plant promoters include the ethanol induced promoter of Caddick et al (1998) Nature Biotechnology 16: 177-180.

If desired, selectable genetic markers may be included in the construct, such as those that confer selectable phenotypes such as resistance to antibiotics or herbicides (e.g. kanamycin, hygromycin, phosphinotricin, chlorsulfuron, methotrexate, gentamycin, spectinomycin, imidazolinones and glyphosate).

The present invention also provides methods comprising introduction of such constructs comprising appropriate suppressors and heterologous sequences into a plant cell and/or induction of expression of a construct within a plant cell, by application of a suitable stimulus e.g. an effective exogenous inducer.

Nucleic acid can be introduced into plant cells using any suitable technology, such as a disarmed Ti-plasmid vector carried by Agrobacterium exploiting its natural gene transfer ability (EP-A-270355, EP-A-0116718, NAR 12(22) 8711-87215 1984), particle or microprojectile bombardment (U.S. Pat. No. 5,100,792, EP-A-444882, EP-A-434616) microinjection (WO 92/09696, WO 94/00583, EP 331083, EP 175966, Green et al. (1987) *Plant Tissue and Cell Culture*, Academic Press), electroporation (EP 290395, WO 8706614 Gelvin Debeyser) other forms of direct DNA uptake (DE 4005152, WO 9012096, U.S. Pat. No. 4,684,611), liposome mediated DNA uptake (e.g. Freeman et al. *Plant Cell Physiol.* 29: 1353 (1984)), or the vortexing method (e.g. Kindle, *PNAS U.S.A.* 87: 1228 (1990d) Physical methods for the transformation of plant cells are reviewed in Oard, 1991, *Biotech. Adv.* 9: 1-11.

Ti-plasmids, particularly binary vectors, are discussed in more detail below.

Agrobacterium transformation is widely used by those skilled in the art to transform dicotyledonous species. However there has also been considerable success in the routine production of stable, fertile transgenic plants in almost all economically relevant monocot plants (see e.g. Hiei et al. (1994) *The Plant Journal* 6, 271-282)). Microprojectile bombardment, electroporation and direct DNA uptake are preferred where Agrobacterium alone is inefficient or ineffective. Alternatively, a combination of different techniques may be employed to enhance the efficiency of the transformation process, eg bombardment with Agrobacterium coated microparticles (EP-A-486234) or microprojectile bombardment to induce wounding followed by co-cultivation with Agrobacterium (EP-A-486233).

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

Thus various aspects of the present invention provide a method of transforming a plant cell involving introduction of a suppressor-based construct as described below into a plant tissue (e.g. a plant cell) and causing or allowing recombination between the vector and the plant cell genome to introduce a nucleic acid according to the present invention into the genome.

This may be done so as to effect transient expression. Alternatively, following transformation of plant tissue, a plant may be regenerated, e.g. from single cells, callus tissue or leaf discs, as is standard in the art. Almost any plant can be entirely regenerated from cells, tissues and organs of the plant. Available techniques are reviewd in Vasil et al., *Cell Culture and Somatic Cell Genetics of Plants, Vol I, II and III, Laboratory Procedures and Their Applications*, Academic Press, 1984, and Weissbach and Weissbach, *Methods for Plant Molecular Biology*, Academic Press, 1989.

The generation of fertile transgenic plants has been achieved in the cereals rice, maize, wheat, oat, and barley (reviewed in Shimamoto, K. (1994) *Current Opinion in Biotechnology* 5, 158-162.; Vasil, et al. (1992) *Bio/Technology* 10, 667-674; Vain et al., 1995, *Biotechnology Advances* 13 (4): 653-671; Vasil, 1996, *Nature Biotechnology* 14 page 702).

Regenerated plants or parts thereof may be used to provide clones, seed, selfed or hybrid progeny and descendants (e.g. F1 and F2 descendants), cuttings (e.g. edible parts) etc.

Use in Mammals

Suppressors may be used to enhance the activity of viral vectors or other vectors used in gene therapy (c.f. evidence of RNA interference in mouse embryos, Wianny F et al (2000) Nature Cell Biology 2 pp70-75). Such vector may be based on any appropriate vector known to those skilled in the art. See for instance the disclosure of European patent application 909052736.3 (VICAL). Known viral vectors include HSV, vaccinia or adenovirus (see Principles of Gene Manipulation (1994) 5th Edit. Old and Primrose 5th Edition, Blackwell Scientific Publications). Viral vectors for use in gene therapy are also discussed by Vile (1997) Nature Biotechnology 15: 840-841. A non-viral gene therapy approach is discussed by Sebestyen et al (1998) Nature Biotechnology 16: 80-85. The use of a variety of gene therapy delivery systems (including HSV VP22) is discussed by Fernandez & Baylay (1998) Nature Biotechnology 16: 418-420 and references therein.

In preferred forms the suppressors may be used in conjunction with methods of nucleic acid transfection or lipofection (see e.g. Wiggler M, et al. 1977 Cell 11, 223-232; Ruyssaert J M, et al 1994 Biochem Biophys Res Comm 203, 1622-1628; Biochem Biophys Res Comm 236. 126-129.

Different PTGS Contexts

The invention may be applied in any context in which it is desired to suppress PTGS irrespective of the precise PTGS origin. As discussed above, post-transcriptional gene silencing (PTGS) is a nucleotide sequence-specific defence mechanism that can target both cellular and viral mRNAs. PTGS occurs in plants and fungi stably or transiently transformed with foreign (heterologous) or endogenous DNA and results in the reduced accumulation of RNA molecules with sequence similarity to the introduced nucleic acid (Vaucheret, et al., *Plant J*. 16, 651-659 (1998); C. Cogoni and, G. Macino, *Trends Plant Sci.* 2, 438-443 (1997)).

Specific PTGS instances include: silencing of endogenous genes by use of additional copies of the gene (co-suppression—see, for example, van der Krol et al., (1990) *The Plant Cell* 2, 291-299; Napoli et al., (1990) *The Plant Cell* 2, 279-289; Zhang et al., (1992) *The Plant Cell* 4, 1575-1588, and U.S. Pat. No. 5,231,020); silencing of endogenous genes by insertion of homologous genes; silencing arising from the use of cytoplasmically replicating constructs (W095/34668 (Biosource); Angell & Baulcombe (1997) The EMBO Journal 16,12:3675-3684); systemic silencing of transgenes or endogenous arising from transient presence in the cytoplasm of homologous nucleic acids (and Voinnet & Baulcombe (1997) Nature 389: pg 553), 'self-silencing' of transgenes; virally induced RMD; transgene-mediated homology-dependent, virus resistance etc.

By monitoring the short RNA species (around 25 nt, more preferably about 21-23nt RNA) associated with PTGS, or by monitoring mRNA and\or expressed protein (Nothern or Western Blots) the existence and severity of PTGS can be assessed.

Enhancing Expression

In preferred embodiments, the suppressor is used to enhance expression, particularly the level of translation, of a heterologous or endogenous nucleic acid in a cell, particularly a plant cell. Expression may be enhanced, for instance, by at least about 25-50%, preferably about 50-100%, or more. In certain preferred embodiments in which PTGS may be particularly severe, at least 5, 10, 15, 20, 25, or 50-fold enhancements of expression may be achieved.

Thus the present invention provides methods of or for suppressing PTGS, and enhancing expression of heterologous or endogenous nucleic acids (to produce heterologous or endogenous polypeptides), in cells, which employ the suppressors of the present invention discussed above.

Those skilled in the art, using the information herein, and the transient assay described in the Examples, will be able to assess which of the various suppressors in the PTGS pathway can act synergistically. A further use of the suppressors herein is for the analysis of cellular factors interacting with them, which will allow identification of components of PTGS that would not be accessible by conventional mutagenesis.

Choice of Genes to Enhance

Genes of interest include those encoding agronomic traits, insect resistance, disease resistance. herbicide resistance. sterility, grain characteristics, and the like. The genes may be involved in metabolism of oil, starch. carbohydrates, nutrients, etc. Genes or traits of interest include, but are not limited to, environmental-or stress-related traits, disease-related traits, and traits affecting agronomic performance. Target sequences also include genes responsible for the synthesis of proteins, peptides, fatty acids, lipids, waxes, oils. starches, sugars, carbohydrates, flavors, odors, toxins, carotenoids. hormones, polymers, flavonoids, storage proteins, phenolic acids, alkaloids, lignins, tannins, celluloses, glycoproteins, glycolipids, etc.

Most preferably the targeted endogenous genes in monocots and/or dicots may include those encoding enzymes responsible for oil production in plants such as rape, sunflower, soya bean and maize; enzymes involved in starch synthesis in plants such as potato, maize, cereals; enzymes which synthesise, or proteins which are themselves, natural medicaments such as pharmaceuticals or veterinary products.

Heterologous nucleic acids may encode, inter alia, genes of bacterial, fungal, plant or animal origin. The polypeptides may be utilised in planta (to modify the characteristics of the plant e.g. with respect to pest susceptibility, vigour, tissue differentiation, fertility, nutritional value etc.) or the plant may be an intermediate for producing the polypeptides which can be purified therefrom for use elsewhere. Such proteins include, but are not limited to retinoblastoma protein, p53, angiostatin, and leptin. Likewise, the methods of the invention can be used to produce mammalian regulatory proteins. Other sequences of interest include proteins, hormones, growth factors, cytokines, serum albumin, haemoglobin, collagen, etc.

Expression of Target Genes

Generally speaking, heterologous nucleic acids may be expressed by any appropriate process used in the art. For example, in addition to expression-Amplicons (described above) they may be transcribed or expressed as follows:
(i) transient expression of 'naked' DNA e.g. comprising a promoter operably linked to the heterologous sequence,
(ii) expression from an expression vector, particularly a replicating vector. Generally speaking, those skilled in the art are well able to construct vectors and design protocols for recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press or *Current Protocols in Molecular Biology*, Second Edition, Ausubel et al. eds., John Wiley & Sons, 1992. Viral expression vectors (see below) may be particularly preferred.
(iii) expression from an integrating vector (e.g. a binary vector) which is at least transiently present in the cytoplasm,
(iv) expression from a transgene stably incorporated into the genome of an organism, particularly a plant.

It will be understood that these categories are not mutually exclusive, for instance because an integrating vector may also be an expression vector etc.

Methods for achieving such expression are discussed elsewhere herein.

Formats for Use of Suppressors

Generally speaking, the suppressors may be used to enhance the expression of heterologous or endogenous nucleic acids in the following formats:
(i) expression of the suppressor by infection from a progenitor virus which encodes it,
(ii) expression from a recombinant expression vector, particularly a replicating vector.
(iii) expression from an integrating vector (e.g. a binary vector) which is introduced into the organism,
(iv) expression from a transgene stably incorporated into the genome of an organism, particularly a plant (e.g. constitutively expressed in a transgenic plant), For viral vectors and progenitor viruses, the suppressors may be used to suppress PTGS in plants for which their progenitor viruses are naturally infective or not naturally infective.

Alternatively they may be used in plants or other organisms which are not 'natural hosts'.

Certain virally expressed suppressors have been found to be particularly efficient such as the PVX-based expression vectors employed in certain of the Examples below. Other viral vectors are discussed in U.S. Pat. Nos. 5,316,931 and 5,589,367 (Donsen et al); Takamatsu et al (1990) FEBS Lett 269: 73-76; Hamamoto (1993) Bio/Technology 11: 930-932; Kumagag et al (1993) Proc Natl Acad Sci USA 90: 427-430.

The expression of the suppressor may in each case (as appropriate) be prior to, simultaneous with, or after, the expression of the heterologous or endogenous nucleic acid, provided that in each case the suppressor has the effect of enhancing expression by suppressing PTGS, which PTGS would otherwise occur at a higher level in the absence of the suppressor. The term "in conjunction" covers all of these possibilities.

Multiple copies of a suppressor may be used. Different suppressors may be used together (e.g. in tandem) provided that at least one is a suppressor of the present invention.

Suppressors may be operably linked to inducible promoters in order that their activity may be regulated.

Preferred Formats and Combinations for Enhanced Expression

P25 and Viral Susceptibility

As discussed in the examples below, certain suppressors (e.g. PVX p25) may operate specifically on one aspect of the PTGS pathway. This means they may be more appropriate for enhancing the expression of integrated, optionally stable, transgenes than, say, genes expressed from replicating viral-based constructs (which may initiate PTGS via a different pathway). In the light of the present disclosure those skilled in the art will be able to employ appropriate suppressors in appropriate formats in accordance with their requirements.

Thus in a preferred aspect of the invention there is disclosed use of p25 (or a variant thereof) to specifically enhance expression (particularly translation) of a heterologous or endogenous nucleic acid incorporated into the genome of a plant, wherein local virus induced gene silencing in said plant is substantially unaffected by the enhancement (such that viral resistance is not equivalently compromised by the suppression of silencing).

The effect of the enhancement on virus induced gene silencing and/or viral resistance in the plant can be readily ascertained by those skilled in the art by comparison with a control plant (or group of plants) in which p25 is not present. The severity of viral infection, following inoculation, in each case can be assessed or scored using conventional methods e.g. analogous to those discussed below in the Examples. In this aspect of the invention, it may be expected that some impairment of the virus-response in the plant may occur as a result of the inhibition of any systemic silencing signal in the plant. However the overall effect may be less severe than in those cases where the suppressor causes suppression of both local and systemic silencing.

Amplicons

Combinations of suppressors of the present invention and silencing systems (such as that described in WO99/15682 of Plant Bioscience Limited) or more preferably 'amplicon' systems (such as that described in WO98/36083 of Plant Bioscience Limited) may be used to generate very high levels of expression, greater than those which may be achieved from conventional (non-replicating) transgenes, even in the absence of PTGS.

'Amplicons', as described in WO98/36083, comprise a promoter operably linked to a viral replicase, or a promoter sequence operably linked to DNA for transcription in a plant cell of an RNA molecule that includes plant virus sequences that confer on the RNA molecule the ability to replicate in the cytoplasm of a plant cell following transcription. The transcripts replicate as if they are viral RNAs, and comprise a targeting sequence corresponding to the gene of interest ('the target gene'). Other sequence from the viral RNA may be omitted to give a minimal amplicon.

They may be introduced as stable transgenes into the genome of the same plant by transformation and/or crossing. Alternatively they may be introduced by agroinfiltration for transient expression.

Thus, an amplicon may comprise a transgene DNA construct including a promoter, cDNA of at least part of a viral genome, and a sequence corresponding to the target sequence or its complement, with which it shares enough sequence similarity to interfere with expression e.g. at least 40%, 50%, 60%, 70%, and up to 100% sequence identity.

In the present context the target sequence may be an endogenous or heterologous sequence, and the amplicon is used in conjunction with (see above) an enhancer which may or may not be part of the amplicon construct. Use of amplicons for enhancing expression of heterologous or endogenous nucleic acids therefore forms one embodiment of the present invention.

Thus, where appropriate the suppressor and heterologous nucleic acid may be encoded by the same construct, for example an amplicon construct wherein the (generally full length) heterologous nucleic acid is inserted into an appropriate cloning site.

Alternatively, and preferably, they may be present on different constructs which can be used in conjunction with each other. For instance the amplicon may be con-infiltrated with a binary vector encoding the suppressor as described above.

In certain contexts (e.g. where the target gene is expressed from an expression-Amplicon—see above) it may be preferable that the suppressor is selected to one which prevents PTGS of replicating viral-type constructs. In such contexts p25 may be less preferred. Where p25 is used, it may be desirable that it is not itself expressed from a cytoplasmically replicating construct, so as to minimise the likelihood that it is itself subject to PTGS.

Enhanced Transient Expression from Binary Vectors

As discussed above, the present inventors have discovered that suppressors of PTGS may be used particularly advantageously to enhance expression from constructs introduced (preferably at high levels) into the cells of an organism, which constructs can exist either integrated or non-integrated into the genome (e.g. ectopically) but in either case can give rise to transcribed mRNA. Although not wishing to be bound by any particular mechanism, it is believed that the suppressors can inhibit the degradation of mRNA produced in this way, thereby permitting it to accumulate at very high levels, giving correspondingly high levels of protein. Constructs can be introduced at relatively high copy number (in both integrated and non-integrated form) with strong promoters, and without the inherent moderating effect which may occur when selecting a stable transformant in which a construct is integrated into the genome. As a result the levels of protein produced may far exceed those obtainable by use of methods of the prior art, and will generally exceed the rate in which the protein (which will generally be heterologous to the organism) can be broken down by any host protection mechanisms. The use of suppressors appears to enhance the levels and stability of the mRNA produced from the copies of the target nucleic acid present in the cell.

Thus in one aspect of the invention there is disclosed use of a PTGS suppressor to inhibit degradation of mRNA encoding a target protein generated by transcription from a transiently introduced nucleic acid construct including the target nucleotide sequence operably linked to a promoter, which construct is introduced into the cell of an organism.

The "introduced nucleic acid" will thus include the target as a DNA sequence provided in the form of a construct that is capable of giving rise to an elevated level of a corresponding mRNA when introduced in conjunction with DNA coding for suppressor DNA compared to the level of mRNA production normally associated with i) stable transgene expression of the said DNA sequence and/or ii) the level of mRNA normally associated with a transient expression system employing a binary vector comprising said DNA sequence (in absence of suppressor).

Preferably the cell is a somatic cell present in a tissue of the living organism. Preferably the construct is simultaneously introduced into a number of cells of the organism.

In certain embodiments of the invention, such uses and methods disclosed herein may be employed in organisms which are plants or animals using any suppressor appropriate to the species in question e.g. the RGF-CaM suppressor from plants (this is believed to be a calmodulin-related protein) see Anandalakshmi R, et al (2000) Science 290 [5 Oct.], 142-144) and the following discussion will be understood to apply correspondingly to these. Preferably, however, the organism is a plant, and the suppressor is one discussed above e.g. of viral origin.

Thus in a preferred aspect of the invention, there is disclosed a method of achieving enhanced expression of a target nucleotide sequence in a plant, which method comprises the steps of transiently introducing into plant material at least a first nucleic acid sequence comprising the target nucleotide sequence and at least a second nucleic acid sequence encoding a suppressor of the invention as described above, wherein the first and second nucleic acids are comprised within a single binary vector, or the first and second nucleic acid sequences are comprised within a first binary vector and a second binary vector respectively. The first nucleic acid sequence may comprise two or more target nucleotide sequences. The second nucleic acid sequence may encode two or more suppressors.

As is well known to those skilled in the art, a binary vector system includes (a) border sequences which permit the transfer of a desired nucleotide sequence into a plant cell genome; (b) desired nucleotide sequence itself, which will generally comprise an expression cassette of (i) a plant active promoter, operably linked to (ii) the target sequence and\or enhancer as appropriate. The desired nucleotide sequence is situated between the border sequences and is capable of being inserted into a plant genome under appropriate conditions. The binary vector system will generally require other sequence (derived from *A. tumafaciens*) to effect the integration. Generally this may be achieved by use of so called "agro-infiltration" which uses Agrobacterium-mediated transient transformation. Briefly, this technique is based on the property of Agrobacterium *tumafaciens to transfer a portion of its DNA ("T-DNA") into a host cell where it may become integrated into nuclear DNA. The T-DNA is defined by left and right border sequences which are around* 21-23 nucleotides in length. The infiltration may be achieved e.g. by syringe (in leaves) or vacuum (whole plants). In the present invention the border sequences will generally be included around the desired nucleotide sequence (the T-DNA) with the one or more vectors being introduced into the plant material by agro-infiltration. Nevertheless, it is believed that the suppressing effect operates even though the T-construct may not actually be integrated into the genome, but is present (at relatively high copy number) nonetheless. Preferably the binary transformation vector is based on pBin19 described below (see Materials and Methods; see also Frisch, D. A., L. W. Harris-Haller, et al. (1995). "Complete Sequence of the binary vector Bin 19." Plant Molecular Biology 27: 405-409).

In another preferred aspect of the invention, there is a disclosed a method of achieving enhanced expression of a target nucleotide sequence in a plant, which method comprises the steps of introducing into plant material, at least one nucleic acid construct which is a binary vector comprising the target nucleotide sequence and encoding a suppressor of the invention as described above. The target gene may be endogenous or otherwise to the plant material.

In a further embodiment the method uses a first nucleic acid construct which is a binary vector comprising the target nucleotide sequence in conjunction with a second nucleic acid construct which is a binary vector which encodes the suppressor. This may be advantageous, inter alia, in terms of ease of construction and manipulation.

Preferably the method employs the step of co-introducing the two species of binary vector into the plant (tissue) e.g. by agroinfiltration, syringe or vacuum infiltration.

In one embodiment there is a provided a method of generating a protein, which method comprises the steps of:
(i) introducing into a tissue of a plant a first nucleic acid comprising the target nucleotide sequence and a second nucleic acid encoding a heterologous suppressor of the invention as described above, wherein the first and second nucleic acids are optionally comprised within a single binary vector,
(ii) causing or permitting expression from the nucleic acid, over a period of time, of the suppressor and the target protein, wherein the suppressor inhibits degradation of the mRNA encoding the target protein,
(iii) harvesting, at least, the tissue in which the target protein has been expressed,
(iv) optionally isolating the target protein from the plant.

Thus the suppressors may be transiently expressed from a transgene inoculated into a first population of leaves on a plant and, after harvesting of said leaves, a second or more population(s) of leaves may be inoculated with a transgene in an appropriate transient inoculation system and grown on the plant using the same or different transient suppressors, As a result, the same plant (transgenic or non-transgenic) may be used to continuously produce desired proteins in its leaves by using different suppressors and/or different nucleic acid sequences encoding different desired proteins after each harvesting of the appropriate leaf population. Moreover, the invention further provides for the use of different suppressors and/or different nucleic acid sequences encoding different desired proteins in different leaf populations of the same plant.

The transgene or target gene or other sequence may be endogenous or otherwise to the plant material.

The isolation may be by entirely conventional means, and may or may not entail partial or complete purification. Alternatively the protein may be used in situ.

The plant material or tissue in question can be all or part of a plant (e.g. a leaf, or several leaves). Generally it will comprise somatic cells present in a 'developed' plant (i.e. not a plantlet, or embryogenic or embryonic tissue for regeneration).

The time period may be any period up to or even beyond which the tissue remains viable, or until it is saturated with protein; in general it may be preferred that it is between about 3 to 10 days, more preferably between about 4 to 7 days.

Naturally more than one target gene and\or suppressor may be used in the or each construct, although a single sequence in each case is preferred. Multiple binary vectors (each including one or more sequence e.g. suppressor) may be introduced at high density into the plant material in an single infiltration. This may be useful for producing e.g. multiple subunits e.g. of an enzyme.

One preferred embodiment capitalises on the sustained presence of mRNA in the cell to permit the production of combinations of proteins in a temporally organised manner, whereby there is provided a method of generating proteins in an organism in a defined sequence, which method comprises the steps of:
(i) introducing into a tissue of the plant, two or more nucleic acids each comprising at least one target nucleotide sequence operably linked to a promoter (optionally an inducible promoter) plus a nucleic acid encoding a heterologous suppressor of the invention as described above,
(ii) causing or permitting expression of the suppressor, plus a first nucleic acid encoding a first target protein,
(iii) subsequently causing or permitting expression of a further nucleic acid encoding a further target protein,
(iv) optionally repeating step (iii)
(iv) harvesting, at least, the tissue in which the final target protein has been expressed.

Preferred combinations of proteins are those which form metabolic or catabolic pathways in which proteins (e.g. enzymes) act on a substrate which is the product of an earlier protein in the pathway. Alternatively one of the proteins may itself be a substrate for another. In each case the first target protein of (ii) can be considered to generate a substrate for the subsequent target protein of (iii), and so on. The finally harvested tissue can thus contain a complex product which is not itself directly expressed in the plant.

The creation of such pathways as stable transgenes in plants is extremely complex, possibly requiring the crossing of multiple transgenic plants. By using suppressor enhanced construct expression as described above to confer a number of activities upon the plant tissue in particular order, these problems may be avoided.

As shown in the Examples below (particularly Example 9 onwards) transient expression of the target sequence\suppressor when introduced in this way can give very high levels of target polypeptide over the course of the transient expression period, which will generally be several days, depending on the precise methods and materials employed. By using this method, mRNA levels and polypeptide levels are can be sustained for higher levels, and over longer periods, than would be the case in the absence of the suppressor. For example, in the absence of a suppressor, the fluorescence arising from transiently expressed GFP may persist for 3 to 4 dpi, before decreasing and gradually becoming undetectable at 5-6 dpi. By using one or more suppressors as disclosed herein, this may be extended to 15 dpi. The results herein suggest that the transient nature of the expression may be largely due to PTGS. This effect has been confirmed by monitoring the 21-23 nt RNA associated with PTGS of the target gene, or by monitoring mRNA and\or expressed protein (Nothern or Western Blots).

This effectively makes transient expression a useful tool in many contexts for which it may previously have been considered unsuitable e.g. dependable expression of unstable target sequences.

The method may be particularly preferred in those applications where high levels of expression are required, but where viral constructs (with the requirement for plant 'infection') or stable transgenic plants are undesirable e.g. where a rapid assay is important, or where the sequence in question imparts a lethal phenotype.

Compositions of the constructs discussed above form a further aspect of the invention.

Assay for Novel Suppressors

The methods described above can be employed correspondingly to identify novel suppressors. Thus in one aspect of the present invention there is disclosed a method for identifying a suppressor of gene silencing, which method comprises the steps of introducing into plant material, at least one nucleic acid construct which is a binary vector encoding a reporter molecule and encoding a putative suppressor of PTGS. Preferably, the method uses a first nucleic acid construct which is a binary vector comprising the reporter sequence in conjunction with a second nucleic acid construct which is a binary vector which encodes the putative suppressor.

As described above, in the light of the results disclosed herein it will be expected that suppressor activity will result in more prevalent, plus both enhanced and sustained, levels of expression of the reporter gene. Again, this can be confirmed by direct observation and\or Northern or Western blotting.

The putative suppressor can be selected from any source e.g. plant, viral, mammal etc.

The reporter can be any detectable protein, such as a marker gene, commonly used in the art such as GUS, GFP, luciferase etc. Preferably, the reporter is a non-invasive marker such as GFP or luciferase.

All references discussed herein, inasmuch as they may be required to supplement the present disclosure, are incorporated herein in their entirety by reference.

The invention will now be further described with reference to the following non-limiting Figures and Examples. Other embodiments of the invention will occur to those skilled in the art in the light of these.

FIGURES

FIG. 1 shows the viral and transgene constructs used in Example 9 and others. PVX-GFP and PVX-GF were described previously (Ruiz et al., 1998). Expression of the inserts in the PVX vector is controlled by a duplicated coat protein (CP) promoter. The Replicase ORF is essential for replication of viral RNAs; the 25, 12 and 8 kDa proteins are all strictly required for cell-to-cell movement of viral RNAs; the CP is essential for encapsidation as well as cell-to-cell and systemic movement of viral RNAs. All other viral constructs were based on the PVX-GFP construct coupled to the 35S promoter and nos terminator and inserted into the T-DNA of the pBin19 binary vector plasmid. PVX-GFP-ΔCP carries a deletion spanning the entire CP ORF; PVX-GFP-ΔTGB-ΔCP and PVX-GFP-Δrep-ΔCP are based on PVX-GFP-ΔCP and carry a deletion spanning all the TGB ORFs and an in-frame deletion in the replicase ORF, respectively. The PVX-GFP-Δ12k-ΔCP and PVX-GFP-Δ25k-ΔCP constructs carry deletions into the 12kDa and 25kDa ORF, respectively. PVX-GFP-Δ8k-ΔCP carries a frameshift mutation that prevents translation of the 8kDa ORF. PVX-GFP-25k$_{FS}$-ΔCP carries a frameshift mutation in the 25kDa ORF, indicated by "FS" (see "experimental procedures" for details). The 35S-GFP construct was described previously. The 35S-25k and 35S-25k-ΔATG constructs are based on the PVX 25kDa ORF coupled to the 35S promoter and the 35S terminator and inserted into the T-DNA of pBin19. The start codon of the 25kDa ORF has been removed in 35S-25k-ΔATG, as indicated by "ΔATG". LB and RB indicate left and right border of the pBin19 T-DNA, respectively.

Figure 2:
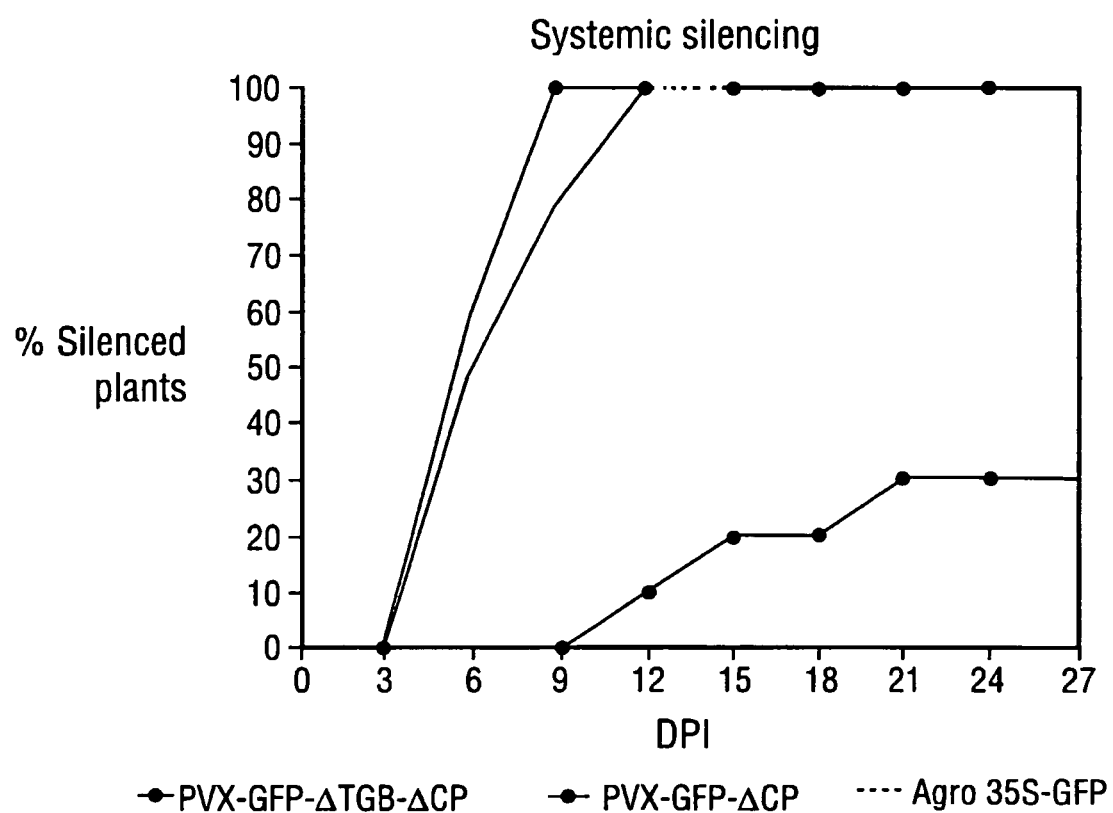

FIG. 2. Effect of the TGB proteins on systemic movement of the GFP silencing signal—kinetics of GFP systemic silencing. Each point in the graph represents the percentage of plants exhibiting GFP systemic silencing as assessed under UV illumination. The average values are from 30 individual plants tested in 3 independent experiments, for each treatment. Plants were scored as silenced even if the systemic silencing was confined to small areas near the veins of a few leaves (i.e. panel B2, at 21 dpi). All of the PVX-GFP-_TGB-ΔCP-inoculated plants showed extensive systemic silencing at 21 dpi.

Figure 3A:
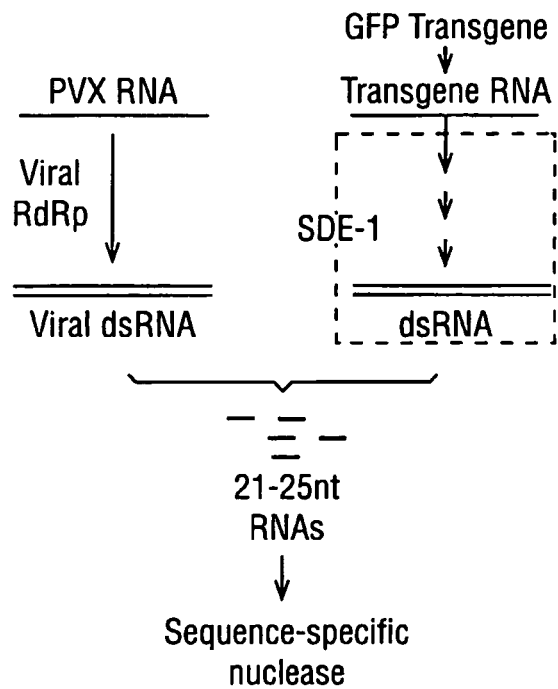

FIG. 3. A model for the mode of action of p25.

(A) The two SDE1-dependent and SDE1-independent branches of the PTGS pathway, as proposed previously (Dalmay et al., 2000). In the SDE1-independent branch, the viral RNA is copied into double stranded RNA (viral dsRNA) by the virus-encoded RNA-dependent RNA polymerase (viral RdRp). Transgene transcripts are processed into dsRNA through a series of steps that involve SDE1. Both viral and transgene dsRNAs are then processed to 21-25nt (now considered to be 21-23nt) RNAs giving specificity to a sequence-specific nuclease that mediates PTGS (Zamore et al., 2000). Note that, in this model, the SDE1-dependent branch is unaffected by viral RNA.

(B) A refined model of PTGS based on the effects of p25 on local and systemic silencing. This model recognizes participation of viral RNA in the SDE1-dependent branch. This branch is involved in production of the systemic PTGS signal and is suppressed by the PVX-encoded p25.

Table I shows "Suppression of PTGS of GFP mRNA caused by various plant viruses." PTGS of the GFP mRNA was induced in transgenic N. benthamiana by Agrobacterium infiltration, as described (17). Following systemic infection, suppression of gene silencing was assessed under UV illumination throughout time and confirmed by RNA gel blot analysis. RNA Samples were taken from either old leaves that had emerged before the virus had spread systemically or from new leaves emerging after virus infection. The total number of plants tested is indicated as well as the phenotype of suppression in leaves (affecting whole tissues or vein centric). Viruses were tested in duplicate independent experiments during the summer and the winter.

Annex I shows a partial sequence of CPDK as used in Example 11.

Annex II shows the sequence of the GFP-RdRp fusion used in Example 13.

EXAMPLES

General Material and Methods

Plant material, Agrobacterium Infiltration and Grafting Procedure

Transgenic N. benthamiana carrying the GFP transgene (line 16c) and the Agrobacterium infiltration method were described previously (Ref 12,—also Voinnet et al., 1998). For co-infiltrations, equal volume of both Agrobacterium cultures (OD$_{600=1}$) were mixed before infiltration. For single infiltration, cultures containing the 35S-25k construct were also diluted up to OD$_{600=1}$ to avoid toxicity to the plant cells. The Rx-GFP plants resulted from a cross between transgenic N. benthamiana homozygous for the Rx locus (Bendahmane et al., 1999) and line 16c. Graftings were performed according to Palauqui et al., 1997.

PTGS Suppression Assay for Examples 1-8.

A test for silencing suppression was based on a previously described experimental system (12). This system involves transgenic Nicotiana benthamiana carrying a highly expressed GFP transgene that are bright green-fluorescent under ultra violet (UV) illumination. Systemic silencing in these plants was induced by infiltration of lower leaves of transgenic seedlings with a strain of Agrobacterium tumefaciens, as described (17). By 20 days post-infiltration, silencing of the GFP was extensive in all vegetative tissues of the plants, and, consequently, they appeared uniformly red under UV illumination. At this stage, there was no PTGS in the growing points of the plant and silencing was maintained by being constantly initiated in non silenced cells located near or in the meristems (17). These silenced plants were then infected with a range of plant viruses and, when systemic symptoms were observed, the extent of green fluorescence was assessed under UV illumination. In addition, Northern analysis was performed to assess the level of GFP mRNAs in infected tissues.

More specifically, leaves of seedlings of line 16c were infiltrated with a strain of A. tumefaciens carrying a binary-Ti plasmid vector into which a functional 35S-GFP cassette had been inserted, as reported (17). After 15-20 days, when PTGS of GFP was achieved in the whole plant, a systemic leaf was inoculated with a wild type or recombinant virus. This leaf is referred to as "inoculated leaf". The challenged virus was then allowed to spread in the silenced plant, and two types of leaves were collected at 14 or 20 DPI. "Old leaves" were infected leaves that had emerged before the virus had spread systemically, whereas "new leaves" were those emerging after the virus had moved systemically.

PTGS Suppression Assay for Examples 9.

To demonstrate a role for the signaling of PTGS is a systemic anti-viral defense we designed grafting experiments in which virus movement would be uncoupled from transport of a silencing signal. The experiments used line 16c of Nicotiana benthamiana carrying a highly expressed green fluorescent protein (GFP) transgene. These plants are bright green under ultra-violet (UV) illumination, whereas non-transformed (NT) plants are red due to chlorophyll fluorescence.

Transgene-induced, systemic silencing of the GFP transgene was initiated by localized infiltration of a strain of Agrobacterium tumefaciens carrying a 35S-GFP T-DNA construct (35S-GFP, FIG. 1).

Virus-induced PTGS of the GFP transgene was initiated by infection with a PVX vector carrying 450 nucleotides from the 5' end of the GFP reporter gene (PVX-GF, FIG. 1).

The rootstocks in these experiments were GFP transgenic plants that had been inoculated with PVX-GF five days previously. These plants exhibited the early signs of PTGS of GFP. The scions carried a GFP transgene together with the Rx gene that confers extreme resistance against PVX. The presence of Rx would prevent replication of PVX-GF in the scions but should have no effect on systemic transport of a silencing signal.

Wild Type Viruses

Isolates of AMV, FOMV, NMV, NVX, VMV and TBSV were obtained from the JIC collection (UK). CPMV was obtained from George Lomonosoff at JIC (UK). ACMV was obtained from John Stanley at JIC (UK). TRV-PPK20 was obtained from John Bol (Leiden University, Netherlands). Other viruses and references were as follows: TMV-U1 (18), PVX-UK3 (19), $PVY_N$ and CMV (12), TBRV-W22 (8) and RYMV-N (20).

Recombinant Viruses (i) The P1 protein sequence of a rice yellow mottle virus isolate from Nigeria (20) was amplified using the following 5' phosphorylated primers; ATG ACT CGG TTG GAA GTT C3' (SEQ ID NO:5) for the intact protein (P1) and ATC ACA CGG TTG TAA GGT TC3' (SEQ ID NO: 4) for an untranslatable protein (mP1). The phosphorylated downstream primer used for amplification was CAT CCC GTG TCA GTC TG (SEQ ID NO: 3). The two PCR fragments were cloned into the EcoRV site of the PVX vector (p2C2S) (19). The orientation of RYMV PCR fragments was confirmed by colony-PCR using antisense primer in the vector sequence at the 3' end of the p2C2S multiple cloning site (GTA GTT GAG GTA GTT GAC CC) (SEQ ID NO: 6) and the two sense RYMV 5' primers described above.

(ii) PVX-AC2 and PVX-mAC2: see (21).

(iii) PVX-HS142 and PVX-HS160: see (22)—referred to as PVX-19k and PVX-m19k herein.

The various PVX-GFP derivatives used in Example 9 onwards were based on pPVX204 which is a PUC19-based vector in which the full length PVX vector is inserted between the 35S promoter and the Nos terminator. The construct referred here to as PVX-GFP is a derivative of pPVX204 carrying the mGFP5 insert from pBin-35-mGFP5 (Ruiz et al., 1998). PVX-GF was derived from PVX-GFP. The entire coat protein ORF was removed from PVX-GFP by digestion with SalI and XhoI and subsequent religation, leading to PVX-GFP-ΔCP. PVX-GFP-ΔTGB-ΔCP was generated by digestion of PVX-GFP-ΔCP with AvrII and EagI, which removed the 3' end of the replicase ORF, the entire TGB and the 3' end of the GFP5 ORF. To restore the replicase and GFP functions, a 3-way ligation was performed with two DNA fragments that had been PCR amplified from PVX-GFP-ΔCP and digested as described below. Amplification with 5'-GCACA-GATTTTCCTAGGCACGTTATC (SEQ ID NO: 7) and 3'-GAAAGAAATTGGgccggctcttgaac (SEQ ID NO: 8) (EagI site underlined) led to a DNA fragment corresponding to the 3' end of the replicase ORF that was subsequently digested by AvrII and EagI; amplification with 5'-cagaaaccg-gccgctagcGGGCCATTGCCG (EagI site underline) (SEQ ID NO: 9) and 3'-TGTACTGCTTGAGATTTACAGCT (SEQ ID NO: 10) led to a DNA fragment corresponding to the 5' end of GFP5 ORF that was subsequently digested by EagI. PVX-GFP-Δrep-ΔCP and PVX-Δrep-GFP-ΔTGB-CP were generated by digesting PVX-GFP-ΔCP and PVX-GFP-ΔTGB-ΔCP, respectively, with BglII and religation, generating a 1729-nt deletion in the replicase ORF. Individual TGB mutants were generated by introducing previously characterized mutations into the PVX-GFP-ΔCP background. PVX-GFP-12k-ΔCP was made by inserting an ApaI-BstBI restriction fragment of PVX-GFP-12D (Verchot et al., 1998) into ApaI-BstBI digested PVX-GFP-ΔCP. PVX-GFP-Δ8k-ΔCP was generated by inserting an ApaI-BstBI restriction fragment of pTXS-8K-GFP (kindly provided by Simon Santa Cruz, SCRI, Dundee) into ApaI-BstBI digested PVX-GFP-ΔCP. pTXS-Δ8K-ΔGFP has a mutation in the start codon (M->T) of the 8kDa protein that also introduces an in-frame STOP codon without altering the coding capacity of the overlapping 12kDa protein ORF. PVX-GFP-Δ25k-ΔCP was generated from pTXS-GFP-ΔApa/Apa that has a 354-nt deletion in the 25kDa ORF, between an ApaI site inserted by mutation of nucleotides 4588-4591 in the PVX genome and an ApaI site existing naturally at position 4945. The deletion was then introduced as an AvrII-BstBI fragment into AvrII-BstBI digested PVX-GFP. Finally, the PVX-GFP-25kFS-ΔCP construct was generated by inserting an AvrII-BstBI restriction fragment from pTXS-GFP3A (kindly provided by Simon Santa Cruz, SCRI, Dundee) into AvrII-BstBI digested PVX-GFP-ΔCP. pTXS-GFP3A carries a 4bp deletion, resulting from removal of the 3' overhang (T4 DNA polymerase) of an ApaI digestion at nucleotide 4945 in the PVX genome. This mutation causes a frameshift in the 25kDa ORF starting at amino acid 154 and introduces an in-frame STOP codon at amino acid 159, leading to a truncated protein (C-terminal deletion of 73 amino acids). Constructs carrying fragments of endogenous genes (PDS and Rbcs) were all derivatives of the above vectors. The unique PmlI blunt site in GFP5 was used to clone the corresponding inserts (see figure legends). All the constructs described here were confirmed by sequencing and inserted as SacI fragments into the T-DNA of the pBin19 vector plasmid (Bevan, 1984). The 35S-25k and 35S-25k-ΔTG constructs are based on pBin19 containing the 35S expression cassette of pJIT61 (JIC). The 25kDa inserts were PCR fragments amplified from pPVX204, using the PFU polymerase (Promega). For 35S-25k-ΔTG, the start codon was omitted in the forward primer. Both constructs were confirmed by sequencing.

General Procedures

In-vitro transcription reactions to produce infectious recombinant PVX RNAs and inoculation were as described (19). Northern analysis was as previously (13).

RNA isolation and Northern analysis of high and low molecular weight RNAs were as described (Dalmay et al., 2000). Viral inocula of PVX-GFP and PVX-GF were described previously (Ruiz et al., 1998).

Visual detection of GFP was as described (12). Close ups were obtained using a LEICA MZFLIII dissecting stereomicroscope coupled to a fluorescence module. The filter set used for GFP imaging was the GFP-plus fluorescence set from Leica (excitation 480 nm, dichromatic beam splitters, 505 nmLP, Barrier filter 510 nmLP). Photographs were produced using LEICAMPS60 device coupled to the stereomicroscope.

Example 1

Suppression of Gene Silencing by Diverse Plant Viruses

Certain of the viruses tested suppressed gene silencing in *N. benthamiana* (Table 1). With several viruses, suppression occurred in old leaves (OL) that had emerged before the virus had spread, as well as in new emerging leaves (NL). This was reminiscent of the pattern of silencing suppression previously described for PVY (12). In contrast, tomato bushy stunt virus (TBSV) only suppressed gene silencing in new emerging tissues, as was previously reported for CMV (12). Foxtail mosaic virus (FoMV), alfalfa mosaic virus (AMV) or tobacco black ring virus (TBRV) were like PVX in that they were fully infectious but did not have any effect on GFP silencing (but see Example 9 below). Based on these results it would appear that PTGS suppression is a property of a variety of plant viruses. However, since the spatial pattern and degree of suppression varied extensively between viruses, it was likely that different mechanisms are involved.

The results may suggest that virus-encoded suppressors of gene silencing have distinct modes of action, and are targeted against distinct components of the host gene silencing machinery. It is unlikely that these differences reflect the tissue tropism of these viruses because similar patterns were reproduced when various suppressors were expressed from a PVX vector that has been shown to express foreign proteins uniformly throughout infected leaves (19). A more likely explanation depends jointly on the mode of action of the suppressor and the component of the gene silencing mechanism that is targeted. For example, if a suppressor can degrade a component required for maintenance of gene silencing, it will have an effect in both new and old leaves. However, if the suppressor blocks synthesis or activation of a component required for silencing, the suppression would be restricted to new emerging leaves where silencing would be established in the presence of the viral suppressor. In old leaves, the component would have been formed in the absence of the suppressor and, consequently, would be unaffected when the virus would infect the plant.

Example 2

Suppression of PTGS by the Geminivirus-Encoded AC2 Protein

Tissues were photographed under UV illumination from a dissecting microscope at 15 DPI. The red tissue corresponds to chlorophyll fluorescence under UV, and thus is indicative of gene silencing of GFP. The green fluorescent tissue that sometimes appears yellow is from expression of GFP, and thus indicates suppression of gene silencing. As shown in Table 1, infection of African cassava mosaic geminivirus (ACMV) led to suppression of GFP silencing at about three weeks post-inoculation in both fully expanded and new emerging infected tissues.

Northern analysis was performed in RNA extracted at 20 DPI from either mock infected, non-silenced (NS) or silenced (S) *N. benthamiana* infected with ACMV, PVX-AC2, PVX-mAC2 or PVX. RNA samples were taken either from inoculated leaves, old leaves that had emerged before the virus had spread systemically, or from new leaves emerging after virus infection (NL). Equal amounts of each RNA sample (10 µg) were assayed by RNA gel blotting, using a $^{32}$P-labelled GFP cDNA as probe. Ethidium bromide staining of ribosomal RNA (rRNA) showed equal loading of the samples. The Northern analysis revealed that GFP mRNA levels were high in both types of tissues, and that suppression also occurred in inoculated leaves, although to a lower extent. Therefore, these results were consistent with a suppressor of PTGS encoded in the ACMV genome.

To identify this putative suppressor, we exploited previous findings that a PVX vector expressing the AC2 protein (PVX-AC2) produced necrotic symptoms that were much more severe than those of wild type PVX, suggesting that AC2 suppressed a host defense mechanism. Individual sequences were inserted into the P2C2S PVX vector using the ClaI-EcoRV-SalI multiple cloning site (19), leading to "PVX-X" (e.g. PVX-AC2). Expression of the inserts and the PVX coat protein is controlled by duplicated coat protein promoters. Mutant versions of all pathogenicity determinants used in this study were referred to as "mX" (e.g. PVX-mAC2). From the above results, it was likely that AC2 was a suppressor of RMD.

The test of this hypothesis was to infect GFP-silenced plants with PVX-AC2. As a control, plants were also inoculated with PVX-mAC2 in which a single point mutation introduces a premature stop codon in the AC2 ORF (21). At about two weeks post-inoculation, PVX-AC2 infected plants exhibited severe symptoms, as reported (21). Under UV illumination, most of the infected tissues, including leaves that had emerged prior to virus inoculation, were green fluorescent and GFP mRNA levels were similar to those in non-silenced GFP plants. In contrast, PVX-mAC2 did not produce severe symptoms and did not suppress GFP silencing. From these results, we conclude that the AC2 protein encoded in the ACMV genome is a suppressor of maintenance of PTGS in *N. benthamiana*.

Example 3

Vein Specific Suppression of Silencing By the 19K Protein of TBSV

*N. benthamiana* infected with TBSV showed reversion of PTGS at about 3 weeks post-inoculation, when symptoms were fully systemic (Table 1). Again photographs were taken under UV illumination from a dissecting microscope at 20 DPI. As in CMV infected plants the restoration of green fluorescence occurred only in new emerging infected leaves. However, this suppression of silencing was weaker than with CMV, so that the green fluorescence was barely detectable under UV illumination from a hand-held lamp. Also unlike CMV, TBSV only suppressed PTGS in and around the veins. Vein-specific reversion of GFP was more evident when detached, new emerging leaves were observed under a dissecting microscope.

Northern analysis of RNA was performed on samples extracted at 20 DPI from silenced (S) *N. benthamiana* infected with PVX-19K or PVX-m19K. RNA samples were taken either from old leaves or from new emerging leaves. Equal amounts of each RNA sample (15 μg) were assayed by RNA gel blotting, using a $^{32}$P-labeled GFP cDNA as probe.

'Mock' inoculations were run as a dilution series of GFP RNAs from a non silenced plant into total RNA from a non-transformed plant. GFP RNA was diluted to a half (1:2) or to a fifth (1:5) of the reference sample (1:1). Ethidium bromide staining of ribosomal RNA (rRNA) shows equal loading of the samples. The Northern analysis showed that GFP RNAs were more abundant in the new leaves of the infected plants than in old leaves or in mock-inoculated, non-silenced plants. However, the GFP RNA in the new leaves was less than 20% of the level in mock inoculated plants.

It has been reported that the 19K protein of TBSV is a pathogenicity determinant. For example, a PVX vector expressing the 19K protein (pHS142), referred to here as PVX-19K, induced severe symptoms on *N. benthamiana* (22). In addition, inactivation of the 19K protein in TBSV had an attenuating effect on the lethal apical necrotic symptom phenotype that is usually elicited in plants by TBSV (22). Collectively these data show that the TBSV 19K protein possesses attributes of a suppressor of gene silencing. To test this hypothesis, silenced GFP plants were inoculated with PVX-19K. As a control, plants were also inoculated with pHS160 (referred to here as PVX-m19K) carrying a non-translatable form of the 19K protein (22). By 2 weeks post-inoculation, plants infected with PVX-19K exhibited very severe symptoms, whereas PVX-m19K infected plants had mild mosaic symptoms, as reported (22). Suppression of silencing occurred in PVX-19K-infected plants but was only manifested in new emerging tissues and was most pronounced in the veins. However, symptoms of PVX-19K were visible on all areas of the leaves. Similar tissues infected with PVX-m19K remained uniformly red-fluorescent. Northern analysis of RNA extracted from new emerging, infected leaves showed that only low levels of GFP RNAs could be detected in PVX-19K-infected tissues and that GFP RNAs were below the level of detection in PVX-m19K-infected tissues. Taken together, these results suggest that the 19K protein of TBSV is a suppressor of PTGS in *N. benthamiana* that operates in the vicinity of the vein tissues of new-emerging leaves.

Example 4

Other Instances in Which Suppression of PTGS Occurs Preferentially in or Near the Veins The effect of tobacco mosaic virus (TMV) and cowpea mosaic virus (CPMV), type members of the tobamovirus and comovirus groups, respectively were assessed as described above with photographs being taken under UV illumination from a hand-held lamp at 20 DPI. Inoculation of the corresponding viruses onto GFP silenced plants led to suppression of gene silencing that affected both new emerging and already expanded silenced tissues, thus indicating that maintenance of PTGS was alleviated (Table 1). However, as shown previously for TBSV and PVX-19K, suppression was mostly manifested near, or in the veins, with most tissues of the lamina remaining silenced (i.e. red fluorescent), although symptoms of the respective viruses were observed on the whole leaf lamina (data not shown). With both viruses, green fluorescence in the vicinity of the veins was very strong and this effect was clearly apparent under UV illumination from a hand-held lamp.

Northern analysis of RNA was performed with material extracted at 20 DPI from silenced *N. benthamiana* infected with TMV and CPMV. RNA samples were taken either from old leaves or from new emerging leaves. Equal amounts of each RNA sample (15 μg) were assayed by RNA gel blotting, using a $^{32}$P-labeled GFP cDNA as probe. Samples were separated on the same agarose gel and blotted on the same filter that was used in Example, thus allowing the use of the same 'mock' GFP RNA dilution series as a reference. Ethidium bromide staining of ribosomal RNA (rRNA) shows equal loading of the samples. The Northern analysis of RNAs extracted from infected leaves showed that GFP RNA accumulation was restored in those tissues, but at a low level, when compared to the abundance of GFP RNA extracted from similar tissues of non-silenced, non-infected plants. This was probably due to dilution of the vein tissue into the most abundant silenced tissues of the lamina. Therefore, this molecular analysis was consistent with the particular phenotype of silencing suppression observed under UV illumination.

The suppression of silencing in veins, for example with the 19K protein of TBSV, could indicate that this protein is only stable or expressed in the veins, or that it is targeted against a component of the PTGS mechanism that is qualitatively or quantitatively different between vascular and non vascular tissue. Alternatively, the suppressor could be targeted against the systemic signal of PTGS. We have shown that this signal is phloem-transmitted and that, in recipient leaves, it is primarily located in and near the veins (17). Of these alternative explanations for suppression of silencing in veins, we consider that those involving vein-specific components or stability of the suppressors are unlikely because, in all cases, PTGS suppression extended into cells outside the vascular bundle and appeared to reflect movement of the signal rather than a precisely vein-specific silencing process. For this reason, we propose that the suppressors of TMV, CPMV and TBSV are likely targeted against the systemic signal of silencing and may therefore represent a viral adaptation to systemic RMD.

Although TMV, TBSV and CPMV are only able to suppress PTGS in or near the veins, they are nevertheless able to accumulate at a high level throughout the infected leaf. It is likely, therefore, that these viruses have secondary strategies for counteracting the effects of RMD.

Example 5

A Pathogenicity Determinant From Rice Yellow Mottle Virus (RYMV) Suppresses PTGS in the Non-Host *Nicotiana benthamiana* Species RYMV is a sobemovirus exhibiting a very narrow host range. It only systemically infects *monocotyledonous* species belonging to the *Oryzae, Phalaridae* and *Eragrostidae* tribes (23). Recent studies have characterised the P1 protein of RYMV as a pathogenicity determinant in rice (24). To test if it would suppress gene silencing in a RYMV non-host species, the P1 ORF was introduced into the PVX vector and GFP-silenced *N. benthamiana* were infected with the resulting recombinant virus (PVX-P1). As a control, a PVX vector carrying a non-translatable form of P1 (PVX-mP1) was also inoculated. At about two weeks post-inoculation, tissues infected with PVX-P1 exhibited severe chlorosis and white necrosis. Under UV illumination, these tissues, including leaves that had emerged prior to virus inoculation, appeared green fluorescent at 14 DPI, reversion of silencing occurring in both new emerging tissues as well as in old leaves.

Northern analysis of RNA was performed on material extracted at 14 DPI from either mock-infected, non-silenced or silenced *N. benthamiana* infected with PVX-P1 or PVX-mP1. RNA samples were taken either from old leaves or new emerging leaves. Equal amounts of each RNA sample (10 μg) were assayed by RNA gel blotting, using a $^{32}$P-labeled GFP cDNA as probe. Ethidium bromide staining of ribosomal RNA (rRNA) shows equal loading of the samples. In young infected tissues, GFP mRNA levels were similar to those in non-silenced GFP plants. GFP mRNAs could also be detected in infected leaves that had emerged prior to virus inoculation, although to a lower extent. In contrast, neither severe symptoms nor reversion of GFP silencing was caused by PVX-mP1-infection. From this data, we conclude that the P1 protein of RYMV is a suppressor of maintenance of PTGS in *N. benthamiana*, although it is encoded in the genome of a virus that is not infectious on *Nicotiana* species.

Example 6

Variations in the Ability to Suppress PTGS in *N. benthamiana* Between Highly Related Members Of The Potexvirus Group.

Northern analysis of RNA was performed on material extracted at 20 DPI from silenced *N. benthamiana* infected with either VMV, NMV, NVX or PVX. RNA samples were taken either from old leaves or from new emerging leavess. Equal amounts of each RNA sample (15 μg) were assayed by RNA gel blotting, using a $^{32}$P-labeled GFP cDNA as probe. Samples were separated on the same agarose gel and blotted on the same filter that was used in Example 3, thus allowing the use of the same 'mock' GFP RNA dilution series as a reference. Ethidium bromide staining of ribosomal RNA (rRNA) showed equal loading of the samples.

Based on the Northern Analysis, PVX and FOMV, both members of the potexvirus group, had no effect on PTGS of GFP in *N. benthamiana* (Table 1).

In contrast, infection with other potexviruses, narcissus mosaic virus (NMV), nandina virus X (NVX) and viola mosaic virus (VMV), led to suppression of gene silencing (measured 20 DPI) in *N. benthamiana*. This suppression was manifested in leaves that were expanded prior to inoculation as well as in young developing tissues (i.e. Reversion of silencing occurs in both new emerging tissues as well as in old leaves) and was photographed under UV illumination from a dissecting microscope at 20 DPI. The suppression was as strong as with Hc-pro, 2b and AC2 and the levels of GFP mRNA in infected tissues were similar to those in mock inoculated, non-silenced plants.

The inocula of these related viruses had been quantified using the local lesion host *Chenopodium amaranticolor* (25) and diluted, so that they would be comparable to a PVX inoculum used as an internal reference (40 lesions per leaf). Following infection, we confirmed that these viruses gave similar types of symptoms. Thus, the variation in the suppressor of silencing activity reflected intrinsic properties of the viruses rather than the degree of infection. Surprisingly the variable suppressor activity did not correlate with the nucleotide sequence similarity of these viruses. PVX and FOMV, which did not suppress silencing, are only distant relatives. In contrast, NVX and VMV, which produced strong suppressors, are respectively 93% and 97% identical to PVX at the nucleotide level, based on sequence analysis of a region spanning the coat protein and the 3 movement proteins (A. Bendhamane and D.C. Baulcombe, in preparation). NMV, which also produced a suppressor, is only a distant relative of PVX. Therefore, there is extreme variation in the ability to suppress PTGS in closely related members of a single virus group.

Example 7

Use of AC2 and P1 as Suppressors of PTGS

Wild type *N. benthamiana* and *N. tabaccum* are transformed with T-DNA containing a 35S-nos expression cassette (17) in which a cDNA of the P1 or the Ac2 protein is inserted using standard laboratory techniques. Stable transformants are generated by Agrobacterium *tumefaciens* leaf disk inoculation (Horsch, R. B., Fry, J. E., Hoffmann, N. L, Eicbholtz, D., Rogers, S. G., and Fraley, R. T. (1985). A simple and general method of transferring genes into plants. Science 227,1229-1231.) and those exhibiting high levels of expression, as assessed by Northern analysis, are selected for testing for PTGS suppression. The PTGS suppression test is performed by taking *N. benthamiana* transformants homozygous for P1 or Ac2 and crossing them with homozygous GFP transgenic *N. benthamiana* (Ruiz, M. T., Voinnet, 0., and Baulcombe, D. C. (1998). Initiation and maintenance of virus-induced gene silencing. Plant Cell 10, 937-946). F1 plants are then infected with PVX-GFP, in order to activate virus induced gene silencing (VIGS) of GFP mRNA (Ruiz et al supra). The suppression by Ac2 and P1 of VIGS of GFP in the F1 crosses demonstrates that both proteins are functional suppressors of PTGS when expressed transgenically. Likewise an absence of systemic silencing of GFP in these crosses demonstrates that both P1 and AC2 prevent transgene induced gene silencing of the GFP mRNAs.

Example 8

Suppression of Amplicon-Mediated Gene Silencing

The *N. tabaccum* transformants described in the Example above are crossed with a transgenic *N. tabaccum* line containing a transgene of the PVX-GUS amplicon (Angell, S. M., and Baulcombe, D. C. (1997). Consistent gene silencing in transgenic plants expressing a replicating potato virus X RNA. EMBO J. 16, 3675-3684). The amplicon line exhibits consistent PTGS of the PVX-GUS RNA and, as a consequence, the GUS protein is not produced. However, the amplicon/P1 or amplicon/Ac2 crosses exhibit high levels of GUS expression, as assessed by histochemical staining of leaves (Jefferson, R. A., Kavanagb, T. A., and Bevan, M. W. (1987).GUS fusions: B-glucuronidase as a sensitive and versatile gene fusion marker in higher plants. EMBO J.6, 3901-3907.) and Northern analysis. PTGS of the amplicon is reduced by the P1 and AC2 proteins, and high levels of GUS protein are produced as a consequence of PVX replication. The plants are symptomless, as in the initial PVX-GUS amplicon line, indicating that the high level of PVX replication is supportable by the plant cells.

Example 9

PVX p25 as a Suppressor of PTGS

A factor in the PVX genome prevents systemic silencing Transgenic scions carrying either the GFP transgene or both the GFP and the Rx transgenes were wedge-grafted onto the rootstocks. Graft-transmission of GFP silencing was then scored under UV illumination throughout time. By 20 days after grafting, PTGS of GFP was extensive in the rootstocks, as indicated by loss of green fluorescence under UV illumination. As expected, there was no spread of PVX-GF into the Rx/GFP scions, indicated by the absence of PVX symptoms and the failure to detect PVX-GF RNAs by Northern analysis. Also as expected, there was spread of PVX-GF and of gene silencing into the GFP scions without Rx. However, there was no systemic silencing of GFP in the Rx/GFP scions in any of ten grafts tested. The scions remained green fluorescent and the levels of GFP mRNA were high, as in non-infected GFP plants.

The absence of systemic spread of GFP silencing into the GFP/Rx scions could result if Rx was able to interfere with systemic silencing. However, when silencing had been induced in the stocks by Agrobacterium infiltration, there was spread into GFP/Rx scions in 8 out of 10 graftings tested: these scions had lost green fluorescence and GFP mRNA could not be detected. In a further control to assess the effect of Rx on silencing we infiltrated Agrobacterium cells carrying the 35S-GFP T-DNA directly into GFP/Rx scions that had been grafted onto PVX-GF-infected plants. In all five of these tests GFP silencing was induced and spread through the GFP/Rx scions indicating that Rx had no effect either on initiation or systemic spread of PTGS. It seemed likely, therefore, that the failure of systemic silencing to spread out of the PVX-GF-infected stocks was due to a factor, presumably a protein, encoded in the PVX genome.

PVX TGB Protein Prevents Systemic Silencing

To determine whether PVX-encoded proteins are able to prevent or interfere with systemic silencing we carried out experiments with deletion mutants of PVX-GFP (FIG. 1). These mutant viruses would have been confined to the initially infected cell because they were all defective for the coat protein (CP) that is required for cell-to-cell and long distance movement of PVX. If, as predicted, a PVX-encoded protein prevented systemic silencing, PTGS initiated by the corresponding PVX-GFP mutant would be manifested away from the inoculated cells. In contrast, silencing initiated by PVX-GFP constructs carrying mutations in any other open reading frame (ORF) would be restricted to the inoculated area.

We first tested the ability of PVX-GFP-ΔCP and PVX-GFP-ΔTGB-ΔCP (FIG. 1) to induce systemic silencing of the GFP transgene. These constructs are similar to the PVX-GFP vector (FIG. 1), except that there is a deletion in the CP ORFs. In addition to the CP mutation, PVX-GFP-ΔTGB-ΔCP carries a deletion spanning all three ORFs of the triple gene block (TGB). The TGB encodes three proteins that are strictly required, in addition to the CP, for cell-to-cell movement of PVX (Verchot et al., 1998).

In order to generate high titer inocula of these mutant viruses we used the pBin19 Ti-plasmid vector (Bevan, 1984) in which the PVX-GFP constructs were coupled to a 35S promoter. Agrobacterium cultures carrying these constructs were infiltrated into leaves of GFP transgenic plants. Transfer of the T-DNA would allow a high proportion of cells inside the infiltrated area to become infected with the movement defective mutants of PVX-GFP.

At 3 days post inoculation (dpi), with PVX-GFP-ΔCP and PVX-GFP-ΔTGB-ΔCP there was strong expression of GFP manifested as bright green fluorescence in the infiltrated regions (data not shown). However, starting at 5-6 dpi, the infiltrated regions became red-fluorescent, suggesting that local PTGS of GFP had been initiated by both of these constructs. The development of this local silencing was as rapid as in leaves infiltrated with the 35S-GFP construct.

With both PVX-GFP-ΔTGB-ΔCP and 35S-GFP, systemic silencing was initiated in 100% of the GFP plants and developed as quickly and extensively as with the 35S-GFP construct (FIG. 2 graph). In contrast, systemic silencing initiated with the PVX-GFP-ΔCP construct was delayed (FIG. 2 graph), appeared in only 30% of the inoculated plants and, in those plants, was restricted to the veins in a few leaves. Because the difference between PVX-GFP-ΔTGB-ΔCP and PVX-GFP-ΔCP involved the TGB ORFs, these results suggested that one or more of the TGB proteins prevented systemic silencing from the PVX-GFP-ΔCP-infected cells.

The PVX-Encoded 25kDa Protein Prevents Systemic Silencing

Similar experiments were carried out with PVX-GFP-ΔCP derivatives in which the TGB ORFs were mutated individually (PVX-GFP-Δ25k-ΔCP, PVX-GFP-25k$_{FS}$-ΔCP, PVX-GFP-Δ12K-ΔCP and PVX-GFP-Δ8K-ΔCP; FIG. 1).

| Construct | Local silencing | Systemic silencing |
| --- | --- | --- |
| PVX-GFP-Δ8K-ΔCP | 50/50 | 12/50 |
| PVX-GFP-Δ12K-ΔCP | 50/50 | 15/50 |
| PVX-GFP-Δ25k-ΔCP | 50/50 | 50/50 |
| PVX-GFP-25k$_{FS}$-ΔCP | 50/50 | 50/50 |

(3 independent experiments were performed, with assessment made at 21 dpi)

With all of these mutants, the infiltrated region became red-fluorescent, suggesting that there was initiation of local PTGS of GFP. However, the only TGB mutants that produced extensive systemic silencing were those carrying either a deletion (PVX-GFP-Δ25k-ΔCP, FIG. 1) or a frameshift mutation (PVX-GFP-25k$_{FS}$-ΔCP, FIG. 1) in the ORF of the 25kDa protein (p25).

The viruses carrying mutations in the ORFs of the 12kDa and 8kDa proteins (PVX-GFP-Δ12K-ΔCP and PVX-GFP-Δ8K-ΔCP, respectively, FIG. 1) encode a functional 25kDa protein and, like PVX-GFP-ΔCP were poor inducers of systemic silencing. Most of the GFP plants inoculated with these constructs did not exhibit any systemic silencing of GFP. However, as with PVX-GFP-ΔCP, about 25% of the inoculated plants exhibited partial silencing of GFP. At 21 dpi this partial silencing was restricted to the regions in and around the veins of some upper leaves and did not develop further.

In principle, the contrasting silencing phenotypes triggered by the PVX-GFP TGB mutants could be a direct effect of p25. Alternatively, there could be an indirect effect if the mutations affected replication or the ability of these mutants to induce PTGS of GFP in the inoculated leaves. To resolve these alternatives we carried out northern analysis of RNA from the infiltrated leaf tissues at 2.5 and 5dpi, using a GFP-specific probe. Total RNA was extracted at 2.5 and 5dpi from leaves of GFP plants that had been infiltrated with either PVX-GFP-Δ8k-ΔCP, PVX-GFP-Δ12k-ΔCP, PVX-GFP-Δ25k-ΔCP, or water. Northern analysis was carried out on 10 µg of the high molecular weight RNA fraction, to detect accumulation of the PVX-GFP and transgene GFP RNA, using a probe corresponding to the central region of the GFP cDNA. Ethidium bromide staining of the electrophoresed gel showed rRNA loading.

At 2.5 dpi, with PVX-GFP-Δ2K-ΔCP, PVX-GFP-Δ8K-ΔCP and PVX-GFP-Δ25k-ΔCP, the extracts contained four major RNA species detected with the GFP probe. The genomic viral RNA (gRNA) was the least and the viral subgenomic (sg) RNA1 was the most abundant. The sgRNA2 co-migrated with and could not be differentiated from the GFP transgene mRNA. At 2.5 dpi, these RNAs were all abundant in the PVX-GFP-Δ12K-ΔCP, PVX-GFP-Δ8K-ΔCP and PVX-GFP-Δ25k-ΔCP-infected tissues. At 5 dpi, however, with all three TGB mutants, the levels of these RNA species were markedly reduced. This reduction was dependent on the virus because, in mock inoculated tissue, the GFP mRNA was at the same level at 2.5 and 5 dpi. Thus, this change in RNA abundance was likely due to PTGS that was targeted against both viral and transgene GFP RNA species.

As an additional test of PTGS induced by the TGB mutants we assayed for 22-25nt antisense GFP RNAs at 5 dpi. Northern analysis of the low molecular weight fraction was carried out with loading being standardized with ethidium bromide staining and quantification of tRNAs in each sample. The probe used corresponded to the full-length GFP cDNA. In other systems, the relative amount of those small antisense RNAs correlates with the level of PTGS (Hamilton and Baulcombe, 1999; Dalmay et al., 2000)). As expected, these 22-25nt GFP RNAs were absent in the extract of mock-infiltrated leaves. However, in PVX-GFP infected tissues these RNAs were present and their levels were unaffected by mutations in the TGB ORFs. This data indicate that all three TGB mutants were efficient inducers of PTGS of GFP.

Combined, these results show that all of the TGB mutants replicated and activated intracellular PTGS to a similar extent. However, systemic spread of silencing only occurred when the PVX-GFP constructs carried mutations in the p25 ORF. It is unlikely that this block was an RNA-mediated effect because systemic silencing was initiated by a PVX-GFP mutant with a frame-shift mutation in the p25 ORF. Therefore, we conclude that the p25 protein was able to prevent systemic PTGS of the GFP transgene.

Systemic Silencing in Non Transgenic Plants

The experiments described above were not directly informative about the extent of systemic silencing in virus-infected plants because they involved GFP transgenes integrated in the plant genome and in the T-DNA of the infiltrated Agrobacterium. Any virus-induced effects would have been amplified and relayed by these transgenes, as shown previously (Voinnet et al., 1998), so that systemic silencing would have been more extensive than in non transgenic plants. Therefore, to obtain a more accurate picture of the systemic signaling due to virus infection we carried out a series of experiments in non transgenic plants. The PTGS in these experiments was targeted against the endogenous gene encoding the ribulose bisphosphate carboxylase small subunit (rbcs). As shown previously, this gene is a potential target of PVX-induced PTGS but, unlike transgenes, it does not participate in the initiation, amplification or maintenance of the mechanism (Jones et al., 1999). Therefore, it was likely that systemic silencing of rbcs would indicate the extent of signal spread from the virus-infected cells.

The constructs in these experiments were derivatives of PVX-GFP-ΔCP (FIG. 1) in which a 500nt fragment of the rbcs cDNA was inserted into the GFP ORF. These derivatives are collectively referred to as PVX-rbcs-X in which "X" indicates the various mutations carried by each individual construct. The Agrobacterium infiltration procedure was used to inoculate these PVX constructs into one or two expanded leaves of non transgenic plants. Fourteen days later, systemic, new emerging leaves were inspected for silencing of rbcs. Inoculation of the PVX-rbcs-ΔTGB-ΔCP derivative led to systemic silencing of rbcs that was manifested as yellow-green chlorosis in and around the veins of systemic leaves.

In contrast to the extensive GFP silencing, the rbcs silencing remained restricted to the vicinity of the veins and was only evident in leaves that emerged within 10-16 dpi. This phenotype was consistent with the lack of relay-amplification associated with PTGS of the rbcs gene and was likely a direct indicator of the virus-induced signal.

| Construct | Systemic silencing |
|---|---|
| PVX-rbcs-ΔTGB-ΔCP | 35/40 |
| PVX-rbcs-Δrep-ΔTGB-ΔCP | 0/40 |
| PVX-rbcs-Δ12K-ΔCP | 0/40 |
| PVX-rbcs-Δ25k-ΔCP | 36/40 |

As with GFP silencing, the rbcs systemic effect required mutation of the 25kDa ORF (in PVX-rbcs-ΔTGB-ΔCP and PVX-rbcs-Δ25k-ΔCP). A construct in which the 25kDa ORF was intact (PVX-rbcs-Δ12K-ΔCP) did not induce systemic silencing. From these results we conclude that, in the absence of a transgene, a virus-induced silencing signal can move several centimeters from infected cells and is primarily localized in the vicinity of the veins. Importantly, the replication-defective PVX-rbcs-Δrep-ΔCP failed to induce systemic silencing of rbcs. This result suggests that in non transgenic plants, production of the signal is dependent on the replication competence of the viral genome responsible for its induction.

Similar results were obtained with PVX-GFP-ΔCP derivatives targeted against the phytoene desaturase (PDS) gene (wherein a 415-nucleotide fragment from the central region of the phytoene desaturase (PDS) cDNA was inserted into the GFP ORF of the corresponding PVX-GFP derivative—FIG. 1). As for rbcs, the systemic silencing of PDS, manifested as photobleaching, was only transient and localized around the veins of some new emerging leaves. It was also dependent on PVX replication. The PDS mRNA is several orders of magnitude less abundant than the rbcs mRNA. We can therefore rule out that the level of target gene expression influenced the vein pattern and persistence of systemic silencing in non transgenic plants.

Ectopic Expression of p25 and Systemic Silencing

The analyses with mutant PVX did not rule out that other virus-encoded proteins, in addition to p25, are involved in preventing systemic silencing. To address this possibility we induced systemic silencing in the presence of p25 expressed independently of other virus encoded proteins. Induction of systemic silencing was by infiltration of Agrobacterium strains carrying the 35S-GFP construct or, as a reference, with the PVX-GFP-Δ25k-ΔCP construct (FIG. 1). These strains were mixed with a second strain containing either the 35S-25k construct or the 35S-25k-ΔATG construct in which the start codon of the p25 ORF is removed (FIG. 1). To perform the experiment, a culture of an Agrobacterium strain containing the 35S-25k or the 35S-25k-ΔATG construct was mixed (equal volume) with a culture of an Agrobacterium strain containing either the 35S-GFP or the PVX-GFP-Δ25k-ΔCP construct (FIG. 1). The corresponding suspension was then infiltrated into one or two leaves of a young GFP transgenic seedling, and the onset of local and systemic silencing of the GFP transgene was monitored throughout time. The values are from independent experiments involving 10 plants each. "Veins" indicates that systemic silencing was only manifested in the veins of a few leaves at 21 dpi. "Full" indicates extensive systemic silencing of GFP at 21 dpi.

| Construct | Co-infiltrated with | Systemic silencing |
|---|---|---|
| 35S-GFP | 35S-25k | 4/40 (veins) |
| | 35S-25k-ΔATG | 37/40 (full) |
| PVX-GFP-Δ25k-ΔCP | 35S-25k | 1/20 (veins) |
| | 35S-25k-ΔATG | 20/20 (full) |

The construct combinations with 35S-25k-ΔATG induced systemic silencing as rapidly and as extensively as with the 35S-GFP construct alone. In contrast, systemic silencing of GFP occurred in only a few plants that had been infiltrated with the 35S-25k combinations. Moreover, in those plants, systemic silencing was incomplete and was restricted to the veins of a few leaves, as in the experiments involving PVX-GFP derivatives with an intact p25 ORF. From these results we conclude that, of the PVX-encoded proteins, p25 was sufficient to interfere with systemic silencing of the GFP transgene.

Ectopic Expression of p25 and Local Silencing

The effect of p25 on systemic silencing could result from a block of signal production in the infiltrated cells. Alternatively, this protein could prevent movement of the signal out of the cells in which it was produced. To investigate these alternatives we monitored the local effects of p25 on RNA levels and GFP fluorescence in the leaves where PTGS had been initiated. If signal movement was targeted, the local silencing in inoculated cells would be unaffected. However, an effect of p25 on signal production would likely affect initiation of local silencing. Northern analysis of high molecular weight RNAs was performed as follows. Total RNA was extracted at 2.5 and 5dpi from leaves of GFP plants that had been infiltrated with the 35S-GFP construct in combination with either the 35S-25k construct, the 35S-25k-ΔATG construct, or water. Northern analysis was carried out on 10 μg of the high molecular weight RNA fraction, to detect accumulation of the GFP RNA, using a probe corresponding to the full length GFP cDNA. Ethidium bromide staining of the electrophoresed gel was used to show rRNA loading. By 5 dpi, in leaves infiltrated with the (35S-25k-ΔATG+35S-GFP) combination or with the 35S-GFP construct alone, there was loss of GFP fluorescence, as expected, indicating the onset of local PTGS (data not shown). Correspondingly, the levels of GFP RNAs in those tissues were lower than in mock-infiltrated tissues and the GFP 21-23nt antisense RNAs were abundant.

In contrast, infiltration with the (35S-25k+35S-GFP) combination caused the green fluorescence to increase in the infiltrated leaf (data not shown). The GFP RNA was also much more abundant in those tissues than in the mock-infiltrated tissues, presumably because the integrated and the ectopic 35S-GFP transgenes were both expressed.

Correspondingly, the GFP 21-23nt antisense RNAs were more than five times less abundant than in tissues infiltrated with 35S-GFP or with (35S-GFP+35S-25k-ΔATG). Northern analysis of low molecular weight RNAs was carried out to detect accumulation of 21-23nt antisense GFP RNAs in the 5 dpi samples analyzed above. Loading was standardized with ethidium bromide staining and quantification of tRNAs in each sample. The probe used corresponded to the full-length GFP cDNA.

Collectively, these results indicate that ectopic, constitutive expression of p25 prevented transgene-induced silencing of the GFP transgene in the infiltrated region.

When the inducer of silencing was the replicating PVX-GFP-Δ25k-ΔCP construct the effects of p25 were more complex. Northern analysis of high molecular weight RNAs was performed as follows. Total RNA was extracted at 2.5 and 5 dpi from leaves of GFP plants that had been infiltrated with the PVX-GFP-Δ25k-ΔCP construct in combination with either the 35S-25k construct, the 35S-25k-ΔATG construct, or water. In the (PVX-GFP-Δ25k-CP+35S-25k) samples, at 2.5 dpi, the levels of all high molecular weight RNAs were substantially higher than in the control.

This data indicate that p25 caused suppression of PTGS at this early time point. However, by 5 dpi, even in the presence of p25, the target RNAs had all declined to lower levels than at 2.5 dpi.

The GFP mRNA from the transgene was masked by one of the viral subgenomic RNAs but it was clearly less abundant than in the mock-infiltrated tissue. This decline in the levels of target RNAs was observed in at least three independent experiments and indicates that, between 2.5 and 5 dpi, local PTGS triggered by PVX-GFP-Δ25k-ΔCP had overcome the initial effect of p25.

The failure of p25 to prevent PTGS in PVX-GFP-Δ25k-ΔCP-infiltrated tissues was confirmed by the analysis of 21-23nt GFP RNAs. This analysis was performed at 5 dpi, as described above. At 5 dpi, these RNAs were 2.5 times more abundant in the presence of 35S-25k than with 35S-25k-ΔATG, corresponding to the similar difference in PVX-GFP-Δ25k-ΔCP RNAs levels. Thus, these 21-23nt GFP RNAs were likely generated primarily from replicating viral RNAs. In agreement with this idea, there was only a low level of 21-23nt RNAs in tissues that had been infiltrated with the non replicating PVX-GFP-Δrep-ΔCP construct (FIG. 1) together with 35S-25k.

Collectively, these results indicate that the ectopically expressed p25 prevented systemic silencing irrespective of whether the inducer was a non replicating transgene construct (35S-GFP or PVX-GFP-Δrep-ΔCP) or replicating RNA (PVX-GFP-Δ25k-ΔCP). In contrast, local silencing was only suppressed by p25 if the inducer was a non replicating transgene construct. In this situation, the block on PTGS was associated with reduced accumulation of the 21-23nt GFP RNAs and, presumably, was targeted against either synthesis or processing of the precursor of these 21-23nt RNAs.

Two Branches of the PTGS Pathway

Transgene-mediated PTGS in Arabidopsis involves production of short RNA species of about 21-23 nucleotides, and requires an RdRP homologue encoded by Sde1; in contrast, PTGS induced by some viruses appears to be independent of Sde1, although it also involves the short RNA (Dalmay et al., 2000). To explain these findings we proposed that PTGS in plants is a branched variation of the pathway leading to RNA interference in Drosophila. This pathway involves processing of double stranded (ds)RNA into the short 21-23nt RNAs that serve as the guide RNA for a sequence-specific nuclease (Zamore et al., 2000).

Our previous suggestion was that, in plants, there are SDE1-dependent and SDE1-independent branches of the PTGS pathway (Dalmay et al., 2000). Both branches are dependent on synthesis of dsRNAs and converge at, or before, production of 21-23nt RNA. The dsRNA in the SDE1-independent branch would be produced through replication of the virus and would thus be dependent on the viral-encoded RdRp (FIG. 3). In this model, the Sde1-dependent branch of the pathway is unaffected by viral RNA.

To interpret the effects of p25 in terms of this model, we differentiate local and systemic PTGS. The local PTGS was suppressed by p25 if it was induced by a 35S-GFP transgene but not if the inducer was the replicating PVX-GFP-Δ25k-ΔCP. Therefore, according to the model (FIG. 3a), p25 would be a suppressor of the Sde1-dependent branch of the pathway. In contrast, systemic PTGS was suppressed by p25 irrespective of whether the inducer was the 35S-GFP transgene or the replicating PVX-GFP-Δ25k-ΔCP. Thus, this effect of p25 on virus-induced systemic silencing is difficult to reconcile with the model presented in FIG. 3a, in which the Sde1-dependent branch of the pathway is a transgene-specific process and is not affected by viral RNA.

In principle, these data could indicate that there are separate pathways, with multiple p25 targets, leading to local and systemic silencing. We cannot rule out that possibility, although it seems unlikely because it requires that a virus-encoded protein would suppress the local PTGS induced by a transgene but not by a replicating virus. Instead, we favour an alternative explanation in which p25 has a single target required for both local and systemic silencing. According to this explanation, the systemic signal would be produced in the SDE1-dependent branch of the pathway and, therefore, would be a precursor of the short RNAs.

Figure 3B:
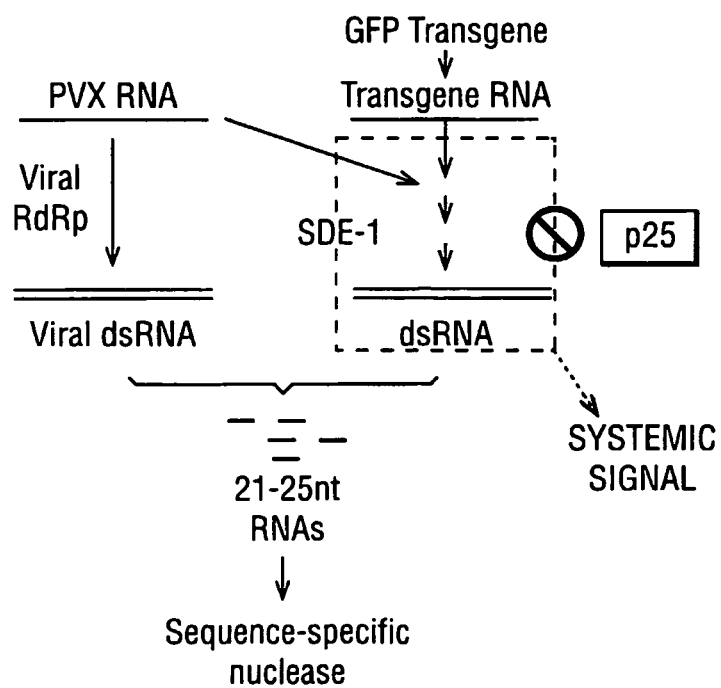

This "single target" explanation involves a refinement of the previous PTGS model (FIG. 3a) in which the SDE1-dependent branch is not influenced by viruses. In the refined model (FIG. 3b), the virus-induced local PTGS would involve the SDE1-independent, p25-insensitive branch of the pathway, as previously. However, the SDE1-dependent, p25-sensitive branch is now recognised as being virus-induced (FIG. 3b). As a result of this change, the model accommodates the finding that systemic signal production is influenced by PVx replication and is suppressed by p25.

A further attraction of this refined model is that it resolves an apparent discrepancy between our results with Sde1 and those of Mourrain et al., (2000) with Sgs2, which is identical to Sde1. In our analysis we found that mutation of Sde1/Sgs2 does not affect susceptibility to tobacco mosaic virus, tobacco rattle virus and turnip crinkle virus (Dalmay et al., 2000) whereas Mourrain and colleagues found that mutations at this locus resulted in hypersusceptibility to cucumber mosaic virus (Mourrain et al., 2000). Presumably, the two sets of data differ because, of the viruses tested, CMV is the only one for which RNA accumulation is strongly limited by systemic PTGS. The other viruses are most likely limited by local PTGS which, as discussed above, is not dependent on Sde1.

Dissection of PTGS Using Viral Suppressors

In Examples 1-8, various viral suppressors involved infection of plants exhibiting transgene-induced PTGS of GFP were characterised. With PVY and other viruses there was an increase of GFP in some or all of the infected tissues, indicating that the corresponding virus encoded a suppressor of PTGS (Brigneti et al., 1998; Voinnet et al., 1999). In contrast, in PVX-infected plants, there was no reversal of PTGS and we originally concluded that this virus does not encode a suppressor.

However, in the light of data presented here, in particular from the ectopic expression of p25, it is clear that PVX does encode a suppressor of PTGS. It is likely that this property of PVX was not evident in the earlier Examples because the p25 protein of PVX and the other suppressors of PTGS, including HcPro of PVY, act on different stages in the gene silencing mechanism.

The clearest indication that Hcpro and p25 target different stages in gene silencing is from their differential ability to suppress virus-induced PTGS. The HcPro suppresses virus-induced PTGS of GFP (Anandalakshmi et al., 1998) whereas it is clear from the present and previous studies that p25 does not. Thus, according to the scheme of FIG. 3b, HcPro should act on PTGS at some point after the convergence of the SDE1-dependent and SDE1-independent branches. Since we have proposed that signal production takes place before the convergence of the two branches, we predict that HcPro would not suppress systemic PTGS. Recent data from grafting experiments confirm this prediction and thereby illustrate how analysis of the different viral suppressors of PTGS can be informative about the underlying mechanisms.

Example 10

Use of Viral Encoded Suppressors of Gene Silencing in Agrobacterium-Mediatted Transient Expression 10.1 The Transient Nature of Agrobacterium-Mediated Gene Expression is Explained by Strong Activation of Post-Transcriptional-Gene-Silencing Targeted Against Sequences Inserted Within the T-DNA The gene encoding the Green Fluorescent Protein (GFP) was cloned under the control of the 35S promoter and Nos terminator. The resulting expression cassette was then inserted into the T-DNA of the pBin19 binary vector. Agrobacterium strain c58cl (Farrand et al (1989) J. Bacteriology 171 pp 5314-5321) carrying the helper plasmid pCh32 (Hamilton et al (1996) PNAS 93 pp9975-9979) was then electroporated with the resulting plasmid. One or several mature leaves of nontransgenic *Nicotiana benthamiana* were infiltrated with a saturated culture of the corresponding Agrobacterium strain that had been previously resuspended in 10 mM $MgCl_2$ and incubated with 100 μM acetosyringone. Infiltration was performed with a syringe, as described previously.

At 2.5 days-post-inoculation (dpi), the infiltrated tissues appeared green fluorescent under illumination from a UV hand-held lamp. This green fluorescence indicated that transfer of the T-DNA from the Agrobacterium into the plant cells has occurred and that transient expression of the reporter gene had been initiated. Starting at 2.5 dpi, infiltrated leaves were removed from the plants at 2 days intervals. Leaf samples were collected up to 11 dpi. Total RNA was extracted from those samples, and Northern analysis was performed on the high and low molecular weight fraction of the extracted RNA, using a probe corresponding to the full-length GFP cDNA.

Analysis of the high molecular weight fraction revealed that the GFP mRNA was abundant at 2.5 dpi. It was still abundant at 4-5 dpi, but at later time points, there was a progressive loss of the signal and at 11 dpi the GFP mRNA was at or below the level of Northern detection. This reduction of GFP mRNA was consistent with the decrease of green fluorescence observed under UV illumination, throughout time. At >4 dpi the green fluorescence started to decrease and was not detectable at >7.5 dpi.

Short 21-23nt RNAs are unique markers of Post-Transcriptional Gene Silencing (PTGS) in plants and RNA interference (RNAi) in *C. elegans* and Drosophila. These processes are mechanistically related and are involved in sequence-specific turnover of RNAs. The 21-23 nucleotide RNA species have been characterised as a core component of the cellular machinery involved in PTGS/RNAi. They are likely to act as specificity determinants of the degradation system.

At 5 dpi, low molecular weight RNA extracted from the infiltrated leaves was separated by electrophoresis with digested GFP plasmid DNA run as approximate molecular size markers (Hamilton and Baulcombe, 1999). RNA and DNA were transferred to a nylon membrane. The membrane was then hybridised with an antisense specific GFP RNA $^{32}$P labelled probe produced by in vitro-transcription of a linear GFP plasmid (Hamilton and Baulcombe, 1999) using T7 RNA polymerase (Promega ). Signal was visualised by phosphorimaging (BAS 1000, Fujix).

The RNA blot showed that high amounts of GFP specific 21-23nt RNAs accumulate in tissues of nontransgenic *N. benthamiana* infiltrated with the 35S-GFP strain of Agrobacterium. Moreover, the abundance of those RNAs species is as high as in transgenic plants exhibiting PTGS of a stably integrated GFP transgene (track 3). It was further confirmed that co-infiltration of the 35S-GFP strain with the p19 strain of Agrobacterium resulted in enhanced GFP mRNA and, consequently protein accumulation (see below). As expected, the level of 23-21nt RNAs was below the detection limit from those samples at 5 dpi.

Combined, these results indicate that transient expression of the GFP transgene in nontransgenic N. benthamiana is prevented by a strong PTGS response activated by the plant. Moreover, the amount of the short RNA species increased in tissues that had been collected at further time points (e.g. up to 11 dpi).

From these data, we conclude that the instability of the GFP mRNA over time and the resulting cessation of green fluorescence in the Agrobacterium infiltrated tissues are caused by very strong activation of PTGS targeted against the gene (e.g. GFP gene) encoded in the T-DNA. This activation of PTGS may explain entirely the transient nature of the Agrobacterium-mediated gene expression.

10.2 Transient Expression of Viral-Encoded Suppressors of PTGS Prevents the Strong Gene Silencing Response to Agrobacterium-Mediated Gene Expression in Nontransgenic N. benthamiana As described above, the HcPro of potyviruses, the 2b protein of cucumoviruses, the Ac2 protein from African Cassava Mosaic Virus, the P1 protein of sobemoviruses and the 19k protein of tombusviruses are viral-encoded suppressors of PTGS. All these proteins were identified as suppressors of PTGS because when expressed from a Potato Virus X (PVX) vector, they restored GFP expression in some or all of the tissues of transgenic plants exhibiting PTGS of GFP. Another protein, the PVX-encoded 25kDa protein was also identified as a suppressor of gene silencing. This protein was shown to prevent production of the PTGS systemic signal and to abolish transgene silencing.

To test if the above suppressors would be effective against the strong PTGS response activated upon Agrobacterium-mediated transient expression in nontransgenic plants, the genes encoding those proteins were cloned under the control of the 35S promoter and 35S terminator. The resulting expression cassettes were then inserted into the T-DNA of the pBin19 binary vector. Agrobacterium strain c58cl carrying the helper plasmid pCh32 were then electroporated with the corresponding plasmids.

In these experiments, the GFP gene was used as a reporter gene, as described in 10.1). The Agrobacterium strain carrying the GFP reporter was mixed (equal volume) with another Agrobacterium strain containing one of the PTGS suppressors mentioned above. After infiltration of leaves of nontransgenic N. benthamiana, appearance and persistence of green fluorescence were assessed under UV illumination. These co-infiltrations were performed with saturated Agrobacterium cultures, ensuring optimal co-transfer of the corresponding T-DNAs.

At 4-5 dpi, it was evident that all of the co-infiltrated tissues were brighter than the tissues that had been infiltrated with the GFP strain alone. This effect was most dramatic with the 19k protein, giving rise to an intense bright green fluorescence. This effect was also very strong, although visually less intense, with the HcPro and 25kDa proteins. The effect of 2b was less strong than the effect of the HcPro and of the 25kDa protein and the effect of Ac2 was itself less strong than the one of the 2b protein. The effect of P1 was the weakest of all but was still significant compared to the control. All these experiments were repeated at least 4 times involving 10 plants for each individual treatment (40 plants per treatment) and gave similar results. The infiltrated tissues did not show any sign of toxicity at those time points.

Western Blot analysis of total proteins extracted from those tissues, using a GFP antibody, is used in order to quantify the observed changes in reporter gene expression. From the observed effects of the 19k, HcPro and 25kDa proteins, GFP expression is expected to be at least 10 fold, and may be 50 fold greater than those in the control tissues.

Not only was GFP expression stronger at the early time points (4-5 dpi), but it was also dramatically sustained over time. For example, strong green fluorescence was still observed in the 19k and HcPro-coinfiltrated tissues at 18 dpi and this fluorescence persisted until leaf senescence. The effect of other suppressors was less persistent over time and was not observed anymore at ≥12 dpi. We also noticed that the 25 kDa coinfiltrated tissues exhibited signs of toxicity which manifested as necrosis around 7 dpi.

To confirm that these effects on GFP expression were due to suppression of PTGS, we assayed for high and low molecular weight RNAs in the sampled tissues. The results were consistent with the fluorescence data. At 5 dpi, the level of GFP 21-23nt RNAs was greatly reduced (more than 6 times) in the 19 kDa, HcPro and 25 kDa-coinfiltrated tissues, when compared to the levels of 21-23nt RNA in control samples (GFP alone). These RNAs were at least 3 times less abundant in the 2b and Ac2-coinfiltrated samples than in the control samples (GFP alone). Surprisingly, only one species (23nt) was strongly affected in the P1-coinfiltrated tissues. At 11 dpi, there was a higher level of 21-23nt RNAs in the tissues coinfiltrated with the 2b, Ac2 and P1 proteins. However, these levels remained low in the 19k-and HcPro-coinfiltrated tissues. At 11 dpi, analysis of the 25 kDa-coinfiltrated tissues was hampered by leaf necrosis (see above).

From these results, we conclude that transient expression of viral encoded suppressors of PTGS dramatically enhances expression of genes delivered transiently by Agrobacterium into nontransgenic plants.

10.3 Additive Effects of the Suppressors of PTGS on Enhancing and Stabilising Transient Expression in Nontransgenic Plants The above experiments were repeated using combinations of suppressors together with the GFP reporter gene. Combining suppressors was achieved simply by mixing individual Agrobacterium cultures together (saturated cultures) and combining them in the GFP culture. Following infiltration of the different mixtures, we found that a higher level of green fluorescence was achieved with the following combinations of suppressors:

(i) 2b+P1 gave greater fluorescence than each individual 2b or P1 infiltration;
(ii) Ac2+P1 gave greater fluorescence than each individual Ac2 or P1 infiltration;
(iii) Ac2+2b combination did not give rise to significant increase of fluorescence, compared to the treatments with 2b or Ac2 alone.

We also tested the effect of combining a mixture of (2b+HcPro+Ac2+P1) together with the GFP reporter culture. In this instance, intense bright green fluorescence (similar to the effect of 19k alone) was observed in the infiltrated tissues and remained visible for up to 18 days.

Western Blot analysis can be performed on those leaf samples to confirm the observed high levels of GFP.

As a further test of the additive/synergistic effect of these suppressors, we analysed the levels of 21-23nt RNAs in the (2b+HcPro+Ac2+P1) samples. At 5 dpi, these RNAs species were at or below the level of detection, in accordance with the fluorescence data.

However, it is already evident that enhanced gene expression can result from the combinations of suppressors of PTGS.

Combining Suppressors of PTGS With a Minimal PVX-GFP Amplicon in the Agrobacterium Transient Expression System A PVX-GFP construct, as described in the earlier examples, was engineered so that the Coat protein Open reading frame was removed from the viral genome, thus preventing virus movement in the plant. This construct was then cloned under the control of the 35 promoter and Nos terminator and subsequently introduced in the T-DNA of pBin19. The plasmid was then inserted into the T-DNA of the pBin19 binary vector. Agrobacterium strain c58cl carrying the helper plasmid pCh32 were then electroporated with the plasmid.

Then, we combined the minimal PVX-GFP amplicon with various suppressors of PTGS as described in 3) and introduced the corresponding cultures in leaves of nontransgenic *N. bemthamiana*. We found that extremely bright green fluorescence was generated in the coinfiltrated tissues. The green fluorescence was stronger than when the 35S promoter was used to drive the GFP marker gene in combination with the suppressors of PTGS (as described in 2) and 3)). This result suggests that silencing, which is normally strongly activated by the PVX amplicon, was alleviated by the suppressors and that strong expression could occur through viral replication, synthesis and translation of the sgRNA driving the GFP reporter gene.

Example 11

Use of Transient Expression and Suppressors of PTGS to Enhance Protein Synthesis in Nontransgenic Plants The two following examples illustrate how the use of suppressors of gene silencing (here the p19 protein of TBSV) can dramatically enhance and sustain protein accumulation in transient expression assays. All the experiments described below were performed in nontransgenic plants.

11.1 Expression of a Plant Gene CDPK

The aim of this experiment was to transiently express and detect a truncated form of a tobacco homologue of a tomato Calcium-Dependent Protein Kinase (CDPK, Romeis et al., 2000). The plant used for over-expression was *Nicotiana benthamiana*.

The cDNA corresponding to a fragment of a tobacco CDPK (Annex I) was inserted as a blunt-end fragment in the SmaI site of the T-DNA of the pBin19 binary vector, using standard procedures, under the control of the 35S promoter and 35S terminator. The corresponding plasmid was then electroporated into electrocompetent Agrobacterium cells (Strain c58cl carrying the hypervirulence plasmid pCh32). The recombinant bacteria (referred to as CDPK strain) were then grown at 28 degrees and one isolated colony was used to produce a saturated culture. This culture was subsequently resuspended in 10 mM $MgCl_2$ and induced with acetosyringone, as described. The induced culture was then brought to an optical density of 0.5 (600 nm).

Following infiltration of leaves of *N. benthamiana* with the Agrobacterium suspension, a time course analysis was performed in order to detect accumulation of CDPK. A similar time course analysis was carried out in parallel from tissues that had been co-infiltrated with a second suspension of Agrobaterium (p19 strain) carrying a pBin19 binary vector in which the p19 cDNA was cloned under the control of the 35S promoter and 35S terminator. This second Agrobacterium culture was used at $OD_{600}=1.0$.

Detection of CDPK was by Western-blot performed on 10 μg of the solubilized membrane fraction of total proteins extracted from the infiltrated tissues. The sequence of the HA epitope tag (Niman et al., 1983) was added to the 3' end of the CDPK cDNA, resulting in a carboxy terminal epitope fusion. The HA antibody (Sigma) was then used for immunodetection, as described (Romeis et al., 2000). Quantification of the signal was performed using the MacBas software (Koshin Graphics Systems Inc, USA).

Results

At early time points (i.e. before 1.5 days post-inoculation) CDPK was not detectable in both experimental set-ups. However, starting at 1.5 dpi, there was a detectable, low level of CDPK produced from the tissues that had been infiltrated with the CDPK strain alone. At 2 dpi these levels were slightly higher (2 times more than the levels at 1.5 dpi). However, at 3 dpi (and up to 5 dpi), the signal was at or below the level of Western-blot detection, indicating that the truncated form of CDPK is unstable. In addition, no signal was detected at any time point in samples extracted from tissues that had been infiltrated with a culture of Agrobacterium cultures carrying an empty pBin19 vector (i.e. with no insert in the T-DNA).

In contrast, at 1.5 dpi, the levels of CDPK from tissues that had been infiltrated together with the p19 strain of Agrobacterium were already at least 3 times higher than the ones in the control experiments described above. At 2 dpi, these levels were at least 5 times higher than those from tissues infiltrated with CDPK alone. Remarkably, although CDPK was undetectable at 3 dpi and at later time points in samples infiltrated with CDPK alone (see above), the levels observed in the p19 co-infiltrated tissues had increased and were at least 10 times higher than the maximum levels observed at 2 dpi in the control samples. Precise quantification of CDPK levels was impaired by the very high amount of protein made in the presence of p19, causing saturation of the signal. It is expected that up to 50 times more protein were produced. These high levels of CDPK were still detectable in samples collected up to 5 dpi or more.

Conclusion

Not only did the addition of p19 enhanced CDPK expression dramatically, it also appeared to prevent degradation of this protein at 3 dpi and later time points. Thus most likely interpretation of this effect is that the p19 protein, by virtue of its anti-silencing property, allowed very high levels of CDPK mRNA to accumulate in the cells. These mRNAs were then translated to such an extent that the plant's protein degradation machinery was saturated, thus allowing the excess unstable protein to peak.

It is likely that the use of saturated cultures of both the p19 and CDPK strains would yield yet higher levels of protein.

11.2 Expression of a Plant Resistance Genes

This example is to illustrate that the effect of p19 on protein synthesis in transient expression assays is not peculiar to CDPK.

In another series of experiments, we assessed the level of accumulation of two tomato proteins expressed transiently in *N. benthamiana* in the presence of p19. These two proteins were the Cf4 and Cf9 resistance gene products, conferring resistance to *Cladosporium fulvum* in tomato.

The principle of these experiments is the same as described above. First, the cDNAs encoding Cf4 and Cf9 were fused with the sequence of a TAP (Rigaut et al., 1999) epitope TAG (resulting in a Carboxy-terminal TAP fusion) and inserted into the T-DNA of pBin19, under the control of the 35S promoter and 35S terminator. The resulting plasmids were then subsequently electroporated into Agrobacterium cells (Strain c58cl carrying the hypervirulence plasmid pCh32) and one colony was used to produce cultures at an optical density of 0.2 (600 nm), referred to as Cf4TAP and Cf9TAP strains, respectively. The p19 strain of Agrobacterium was as described above and was used at $OD_{600}$=1.0.

Detection of Cf4 and Cf9 was by Western-blot analysis performed on 10 µg of the total proteins extracted from the infiltrated tissues. The Peroxidase Anti-peroxidase antibody (sigma) was used for immunodetection as described (Romeis et al., 2000). Quantification of the signal was performed using the MacBas software(Koshin Graphics Systems Inc, USA).

Results

Analysis at 5 days post-infiltration indicated that both Cf4TAP and Cf9TAP were below the level of detection when the corresponding Agrobacterium strains had been infiltrated in the absence of the p19 strain. However, in samples that had been co-infiltrated with the p19 culture, both proteins were readily detectable.

Example 12

Enhancement of Expression of Non-Plant Proteins

In this other set of experiments, a modified cDNA ($GFP_5$, Haseloff et al., 1997) of the Green Fluorescent Protein (GFP) from the jellyfish Aequoria victoria was cloned into the T-DNA of the pBin19 binary vector, under the control of the 35S promoter and the nopaline synthase (nos) terminator, using standard techniques. The resulting vector was then electroporated into electro-competent Agrobacterium (strain C58cl containing the hypervirulence plasmid pCh32). These bacteria were propagated and induced with acetosyringone, as described in examples 10 and 11. A saturated culture (referred to as GFP strain) was used to infiltrate leaves of wild-type Nicotiana benthamiana.

In a parallel set of experiments the GFP strain was mixed (equal volume) with the p19 strain of Agrobacterium (see examples 1-2) and the resulting mix was then infiltrated into leaves of wild-type Nicotiana benthamiana. In this experiment, the culture of the p19 strain was set at an optical density (600 nm) of 2.0.

In addition, two independent, stable Nicotiana benthamiana transformants (line 16c and 8, Ruiz et al., 1998; Voinnet et al., 1998), carrying a highly expressed, single copy GFP transgene were used as a reference in these experiments.

Accumulation of GFP in the infiltrated tissues was assessed throughout time under UV illumination. Quantification of GFP was by immunodetection, using the rabbit anti-GFP antibody from Invitrogen. Samples were harvested at 4 days post-infiltration (dpi), total proteins were extracted and a fraction (30 µl) was analysed by Western-blot, as described (Romeis et al., 2000). Quantification was performed using the MacBas software (Koshin Graphics Systems Inc, USA).

Results

In the tissues infiltrated with the GFP strain alone, there was accumulation of GFP that was visually detectable at 2-2.5 dpi up to 5 dpi. After those time points, there was a decrease in green fluorescence, so that at 7 dpi infiltrated tissues could not be differentiated from mock (water)-infiltrated tissues. At 4 dpi, Western blot analysis performed on two independent samples indicated that despite this rapid decline in GFP expression (transient expression), there was at least 2 times more GFP than in equivalent tissues extracted from the two stable transgenic lines. This result indicates that Agrobacterium-mediated transient expression can lead temporarily to protein levels that are higher than those achieved by stable transformation. As expected, there was no GFP detectable in samples extracted from water-infiltrated tissues.

In the tissues that had been co-infiltrated with the p19 strain of Agrobacterium, there was intense green fluorescence under UV light, that was sustained for more than 11 days. Moreover, Western blot analysis of two independent samples showed that, at 4 dpi, there was at least 10 times more GFP in these tissues than in similar tissues that had been infiltrated with the GFP strain alone (panel A). Moreover, these levels were at least 15 times higher than those produced from the two stable GFP transformants.

Conclusion

As with the Examples above, the effect of p19 was to (i) dramatically enhance and (ii) sustain expression of a foreign protein. The expression was also much higher than in stably transformed plants.

Example 13

Combined Use of Transient Expression and Suppressors Of Gene Silencing Can Enhance Synthesis of Products Resulting From Enzymatic Reactions A fragment of the cDNA of the PVX RNA-dependent RNA-polymerase (RdRp, Malcuit et al., 2000) was fused to the 3' end of the cDNA encoding a modified GFP ($GFP_4$, Haseloff et al., 1997), using standard techniques. A short sequence encoding a cleavage site for the Nia proteinase of Potato Virus Y (PVY) was inserted between both cDNAs (Mestre et al., 2000). The GFP-RdRp fusion cDNA (sequence found below) was inserted into the T-DNA of the pBinY53 binary vector (Mestre et al., 2000). The resulting vector was then electroporated into electro-competent Agrobacterium (strain C58cl containing the hypervirulence plasmid pCh32). These bacteria (referred to as GFP-RdRp strain) were propagated and induced with acetosyringone, as described in examples 1, 2 and 3. This construct should produce a fusion protein [$GFP_4$ amino terminal/RdRp carboxy-terminal] carrying an Nia proteinase cleavage site that should allow the release of free $GFP_4$ by the action of the Nia proteinase. Another strain of Agrobacterium referred to as Pro, contained the pBinYPro binary vector that allows expression of the protease domain from the Nia Proteinase (Mestre et al., 2000).

Results

Infiltration of a culture of the GFP-RdRp strain did not lead to any visible green fluorescence under UV illumination, indicating that the GFP-RdRp protein fusion rendered the GFP inactive. However, when the Pro strain of Agrobacterium was mixed with the GFP-RdRp strain, green fluorescence was detected under UV illimination, from 2 dpi up to 5 dpi. This result indicates that the Nia protease produced by pBinYpro is cleaving the fusion GFP-RdRp protein, allowing the release of free $GFP_4$, hence leading to green fluorescence.

The above assay was then repeated in the presence of the p19 strain of Agrobacterium. For this experiment, cultures of the Pro, GFP-RdRp and p19 strains were mixed together (1:1:1 mix) and accumulatuion of GFP was assessed throughout time. At 3 dpi, there was intense bright green fluorescence in the infiltrated tissues. This fluorescence was sustained at later time points.

Western blot analysis at 3 dpi (as described in example 3) indicated that the levels of free $GFP_4$ produced in the tissues infiltrated with the Pro/GFP-RdRp/p19 combination was at least 6 times higher than in similar tissues infiltrated with the Pro/GFP-RdRp (panel B)9.

Conclusion

The GFP-RdRp protein fusion does not fluoresce under UV light (possibly because the carboxy terminal fusion prevents adequate folding of the $GFP_4$ protein). This interpretation is supported by the fact that green fluorescence was restored in the presence of the Nia proteinase, giving rise to accumulation of free $GFP_4$. Therefore, the high levels of free $GFP_4$ in the Pro/GFP-RdRp/p19 infiltrated tissues are thought to result from enhanced proteolytic activity of the Nia proteinase targeting high levels of its GFP-RdRp fusion protein substrate. It is likely that these high levels of both enzyme and substrate, introduced as T-DNA constructs into the plant cells, resulted from the anti-silencing property of p19. Thus, the GFP-RdRp and Pro mRNAs could accumulate to high levels and were subsequently highly translated. This example illustrates the use of the infiltration/suppression transient assay to rapidly build-up complex biosynthetic reactions in planta and produce high amounts of a particular product.

TABLE 1

Suppression of PTGS of GFP mRNA Caused by Various Plant Viruses

| Virus Group | Virus | Suppression of PTGS | Old leaves/ New leaves | Whole leaf/ Vein centric | Protein | Other known functions* |
|---|---|---|---|---|---|---|
| Alfamovirus | ALMV | 0/9 | — | — | — | — |
| Comovirus | CpMV | 5/6 | OL and NL | Vein centric | ? | — |
| Cucumovirus | CMV | 20/20 | NL only | Whole leaf | 2b | Host specific long distance movement |
| Geminivirus | ACMV | 6/6 | OL and NL | Whole leaf | AC2 | Virion sense gene expression transactivator |
| Nepovirus | TBRV | 0/6 | — | — | — | — |
| Potexvirus | PVX | 0/9 | — | — | — | — |
|  | FoMV | 0/9 | — | — | — | — |
|  | NMV | 8/9 | OL and NL | Whole leaf | ? | — |
|  | NVX | 7/9 | OL and NL | Whole leaf | ? | — |
|  | VMV | 7/9 | OL and NL | Whole leaf | ? | — |
| Potyvirus | PVY/TEV | 10/10 | OL and NL | Whole leaf | HcPro | Genome amplification Viral synergism Longdistance movement Polyprotein processing |
|  | TEV |  |  |  |  |  |
|  |  | Aphidtransmission |  |  |  |  |
| Sobemovirus | RYMV | −+ | −+ | −+ | P1 | Virus accumulation Longdistance movement |
| Tobamovirus | TMV | 4/6 | OL and NL | Vein centric | ? | — |
| Tobravirus | TRV | 7/9 | OL and NL | Whole leaf | ? | — |
| Tombusvirus | TBSV | 7/9 | NL only | Vein centric | 19K | Host-specific spread and symptom determinant |

```
Annex I - sequence of CPDK (SEQ ID NO: 1)
ATGGGGAACACTTGTGTAGGACCAAGCATTTCTAAAAATGGGATCTTTCA

ATCAGTTTCAGCAGCAATGTGGCGATCCCGGTCGCCCGATGACACTGCTT

CCACCACTAATGGTGAAAGTGCTAGAATTGAAACACCAATTTCTGTTAAA

GAACCTGATTCACCTTTGCCAGTTCAAGAGCCACCAGAACAAATGACAAT

GCCTAAGTCAGAAAAGAAAGAAGAAGAAAAAGAACAACCAAAAAAGCCCA

AAAAGCCTGCTGAAATGAAGAGGGTGTCAAGTGCTGGCCTTAGGACAGAT

TCTGTGTTACAAAAGAAAACTGGAAACTTAAAGGAGTTTTTCAGTATAGG

AAAGAAATTAGGACAAGGTCAATTTGGAACTACATTTAAATGTGTCGAAA

AGGCAACAGGGAAGGAATATGCTTGCAAATCGATTGCTAAGAGGAAGTTG

TTAACAGATGATGATGTGGAAGATGTTAGAAGGGAAGTACAGATAATGCA

CCATTTGGCAGGACATCCTCATGTTATATCGATAAAAGGTGCTTATGAGG

ATGCTGTAGCTGTTCATGTAGTTATGGAGTTTTGTGCTGGGGGTGAGCTT

TTCGATAGCATTATTCAACGGGGGCACTATACAGAAAGAAAAGCAGCTGA

GCTTACTAGGACTATTGTTGGAGTTGTAGAAGCTTGTCATTCTCTTGGTG

TCATGCATCGTGATCTTAAGCCTGAAAATTTTCTCTTTGTTGATCAGAAG

GAGGATTCACTTCTCAAAGCAATTGACTTTGGGTTATCGATATTCTTCAA

ACCAGGCGACAGATTTACTGATGTTGTTGGCAGTCCATATTATGTTGCAC

CAGAAGTTCTCCGAAAACGTTATGGTCCTGAAGCTGATGTTTCGAGTGCT

GGTGTAATTATCTACATCTTATTAAGTGGAGTACCTCCTTTCTGGGCTGA

AAATGAGCAAGGAATATTTGAACAAGTCCTGCACGGTGATCTTGACTTCA
```

-continued
CGTCAGACCCATGGCCAAGTATTTCAGAAGATGCAAAAGACTTGATGAGG

AGAATGCTCGTTCGAGATCCGAGAAGACGTTTAACTGCACATGAAGTTTT

ATGCCATCCTTGGGTACAAGTTGATGGTGTTGA

Annex II - sequence of GFP-RdRp - (SEQ ID NO: 2)
Bold, small letters: RdRp sequence
Underlined, capital letters: Nia cleavage site sequence
Capital letters: GFP$_4$ sequence
5'atgagtaaaggagaagaacttttcactggagttgtcccaattcttgtt gaattagatggtgatgttaatgggcacaaattttctgtcagtggagaggg tgaaggtgatgcaacatacggaaaacttacccttaaatttatttgcacta ctggaaaactacctgttccatggccaacacttgtcactactttctcttat ggtgttcaatgcttttcaagatacccagatcatatgaagcggcacgactt cttcaagagcgccatgcctgagggatacgtgcaggagaggaccatcttct tcaaggacgacgggaactacaagacacgtgctgaagtcaagtttgaggga gacaccctcgtcaacaggatcgagcttaagggaatcgatttcaaggagga cggaaacatcctcggccacaagttggaatacaactacaactcccacaacg tatacatcatggcagacaaacaaagaatggaatcaaagttaacttcaaa attagacacaacattgaagatggaagcgttcaactagcagaccattatca acaaaatactccaattggcgatggccctgtccttttaccagacaaccatt acctgtccacacaatctgccctttcgaaagatcccaacgaaaagagagac cacatggtccttcttgagtttgtaacagctgctgggattacacatggcat ggatgaactatacaaaTATGAAGTGCACCATCAAGGAAATGACatgGCCA

AGGTGCGCGAGGTTTACCAATCTTTACAGACTCCACCACAAAAACTCTCA

TCCAAGATGAGGCTTATAGAAACATTCGCCCCATCATGGAAAAACACAAA

CTAGCTAACCCTTACGCTCAAACGGTTGAAGCGGCTAATGATCTAGAGGG

GTTCGGCATAGCCACCAATCCCTATAGCATTGAATTCATACACATGCACC

CGCTAAGACCATAGAGAATAAACTTCTAGAGGTGCTTGGTTCCATCCTAC

CACAAGAACCTGTTACATTTATGTTTCTTAAACCCAGAAAGCTAAACTAC

ATGAGAAGAAACCCGCGGATCAAGGACATTTTCCAAAATGTTGCCATTGA

CCAAGAGACGTAGCCAGGTACCCCAAGGAAACAATAATTGACAAACTCAC

AGAGATCACAACGGAAACAGCATACATTAGTGACACTCTGCACTTCTTGG

ATCCGAGCTACATAGTGGAGACATTCCAAAACTGCCCAAAATTGCAAACA

TTGTATGCGACTTAGTTCTCCCCGTTGAGGCAGCCtaac 3'

REFERENCES

1. Depicker, A. & Van Montagu, M. (1997) *Curr. Opin. Cell Biol.* 9, 372-382.
2. Palauqui, J.-C., Elmayan, T., Pollien, J. -M. & Vaucheret, H. (1997) *EMBO J.* 16, 4738-4745.
3. Voinnet, O. & Baulcombe, D. C. (1997) *Nature* 389, 553.
4. Baulcombe, D. C. (1999) *Curr. Opin. Plant. Biol.* 2, 109-113.
5. Baulcombe, D. C. (1996) *Plant Mol. Biol.* 32, 79-88.
6. Ratcliff, F., MacFarlane, S. & Baulcombe, D. C. (1999) *Plant Cell* 11, 1207-1216.
7. Covey, S. N., Al-Kaff, N. S., Langara, A. & Turner, D. S. (1997) *Nature* 385, 781-782.
8. Ratcliff, F., Harrison, B. D. & Baulcombe, D. C. (1997) *Science* 276, 1558-1560.
9. Vance, V. (1991) *Virology* 182, 486-494.
10. Pruss, G., Ge, X., Shi, X. M., Carrington, J. C. & Vance, V. B. (1997) *Plant Cell* 9, 859-868.
11. Anandalakshmi, R., Pruss, G. J., Ge, X., Marathe, R., Smith, T. H. & Vance, V. B. (1998) *Proc. Natl. Acad. Sci. USA* 95, 13079-13084.
12. Brigneti, G., Voinnet, O., Li, W. X., Ji, L. H., Ding, S. W. & Baulcombe, D. C. (1998) *EMBO J.* 17, 6739-6746.
13. Kasschau, K. D. & Carrington, J. C. (1998) *Cell* 95, 461-470.
14. Beclin, C., Berthome, R., Palauqui, J.-C., Tepfer, M. & Vaucheret, H. (1998) *Virology* 252, 313-317.
15. Kasschau, K. D., Cronin, S. & Carrington, J. C. (1997) *Virology* 228, 251-262.
16. Ding, S. W., Li, W.-X. & Symons, R. H. (1995) *EMBO J.* 14, 5762-5772.
17. Voinnet, O., Vain, P., Angell, S. & Baulcombe, D. C. (1998) *Cell* 95, 177-187.
18. Marano, M. R. & Baulcombe, D. (1998) *Plant J.* 13, 537-546.
19. Chapman, S. N., Kavanagh, T. A. & Baulcombe, D. C. (1992) *Plant J.* 2, 549-557.
20. Pinto, Y. M., Kok, R. A. & Baulcombe, D. C. (1999) *Nature Biotech.* 17, 702-707.
21. Hong, Y., Saunders, K. & Stanley, J. (1997) *Virology* 228, 383-387.
22. Scholthof, H. B., Scholthof, K. B. G. & Jackson, A. O. (1995) *Plant Cell* 7, 1157-1172.
23. Bakker, W. (1974) in *Agricultural Research Report No. 829*. (Centre for Agricultural Publishing and Documentation, Wageningen), pp. 152.
24. Bonneau, C., Brugidou, C., Chen, L., Beachy, R. N. & Fauquet, C. (1998) *Virology* 244, 79-86.
25. Matthews, R. E. F. (1991) *Plant Virology* (Academic Press, San Diego, Calif.).
26. Kjemtrup, S., Sampson, K. S., Peele, C. G., Nguyen, L. V., Conkling, M. A., Thompson, W. F. & Robertson, D. (1998) *Plant J.* 14, 91-100.
27. Atkinson, R. G., Bieleski, L. R. F., Gleave, A. P., Jannsen, B. J. & Morris, B. A. M. (1998) *Plant J.* 15, 593-604.
28. Barker, H. (1989) *Ann. appl. Biol* 115, 71-78.
29. Carrington, J. C. & Whitham, S. A. (1998) *Curr. Opin. Plant. Biol.* 1, 336-341.
30. Elmayan, T., Balzergue, S., Beon, F., Bourdon, V., Daubremet, J., Guenet, Y., Mourrain, P., Palauqui, J. C., Vernhettes, S., Vialle, T., Wostrikoff, K. & Vaucheret, H. (1998) *Plant Cell* 10, 1747-1757.
31. Birchler, J. A., Pal-Bhadra, M. & Bhadra, U. (1999) *Nature Genetics* 21, 148-149.

ADDITIONAL REFERENCES

Anandalakshmi, R., Pruss, G. J., Ge, X., Marathe, R., Smith, T. H., and Vance, V. B. (1998). A viral suppressor of gene silencing in plants. *Proc. Natl. Acad. Sci. USA* 95, 13079-13084.

Angell, S. M., Davies, C., and Baulcombe, D. C. (1996). Cell-to-cell movement of potato virus X is associated with a change in the size exclusion limit of plasmodesmata in trichome cells of *Nicotiana clevelandii*. *Virology* 215, 197-201.

Atabekov, J. C., and Taliansky, M. E. (1990). Expression of a plant virus-encoded transport function by different viral genomes. *Adv in Virus Research* 38, 201-248.

Baulcombe, D. C. (1999). Fast forward genetics based on virus-induced gene silencing. *Curr. Opin. Plant. Biol.* 2, 109-113.

Baulcombe, D. C. (1999). Viruses and gene silencing in plants. *Arch. Virol. suppl.* 15, 189-201.

Bendahmane, A., Kanyuka, K., and Baulcombe, D. C. (1999). The Rx gene from potato controls separate virus resistance and cell death responses. *Plant Cell* 11, 781-791.

Bevan, M. W. (1984). Binary Agrobacterium vectors for plant transformation. *Nucleic Acids Res.* 12, 8711-8721.

Brigneti, G., Voinnet, O., Li, W. X., Ji, L. H., Ding, S. W., and Baulcombe, D. C. (1998). Viral pathogenicity determinants are suppressors of transgene silencing in Nicotiana benthamiana. *EMBO J.* 17, 6739-6746.

Carrington, J. C. (1999). Reinventing plant virus movement. *Trends in Microbiology* 8, 312-313.

Carrington, J. C., Kasschau, K. D., Mahajan, S. K., and Schaad, M. C. (1996). Cell-to-cell and long-distance transport of viruses in plants. *Plant Cell* 8, 1669-1681.

Chisholm, S. T., Mahajan, S. K., Whitham, S. A., Yamamoto, M. L., and Carrington, J. C. (2000). Cloning of the Arabidopsis RTM1 gene, which controls restriction of long distance movement of tobacco etch virus. *Proc. Natl. Acad. Sci. USA* 97, 489-494.

Covey, S. N., Al-Kaff, N. S., Langara, A., and Turner, D. S. (1997). Plants combat infection by gene silencing. *Nature* 385, 781-782.

Dalmay, T., Hamilton, A. J., Rudd, S., Angell, S., and Baulcombe, D. C. (2000). An RNA-dependent RNA polymerase gene in Arabidopsis is required for posttranscriptional gene silencing mediated by a transgene but not by a virus. *Cell* 101, 543-553.

Hamilton, A. J., and Baulcombe, D. C. (1999). A novel species of small antisense RNA in post-transcriptional gene silencing. *Science* 286, 950-952.

Haseloff J, Siemering K R, Prasher D C, Hodge S. (1997) Removal of a cryptic intron and subcellular localization of green fluorescent protein are required to mark transgenic Arabidopsis plants brightly. *PNAS* 18;94(6):2122-7.

Jones, L., Hamilton, A. J., Voinnet, O., Thomas, C. L., Maule, A. J., and Baulcombe, D. C. (1999). RNA-DNA interactions and DNA methylation in post-transcriptional gene silencing. *Plant Cell* 11, 2291-2302.

Jorgensen, R. A., Atkinson, R. G., Forster, R. L. S., and Lucas, W. J. (1998). An RNA-Based Information Superhighway in Plants. *Science* 279, 1486-1487.

Kasschau, K. D., and Carrington, J. C. (1998). A counterdefensive strategy of plant viruses: suppression of post-transcriptional gene silencing. *Cell* 95, 461-470.

Lucas, W. J., and Wolf, S. (1999). Connections between virus movement, macromolecular signaling and assimilate allocation. *Curr. Opin. Plant. Biol.* 2, 192-197.

Malcuit I, de Jong W, Baulcombe D C, Shields D C, Kavanagh T A. (2000) Acquisition of multiple virulence/avirulence determinants by potato virus X (PVX) has occurred through convergent evolution rather than through recombination. *Virus Genes;* 20(2):165-72.

Matthews, R. E. F. (1991). *Plant Virology*, 3rd Edition (San Diego, Calif.: Academic Press).

Mestre P., Brigneti G. and Baulcombe D. C. (2000) An Ry-mediated resistance response in potato requires the intact active site of the Nia proteinase from potato virus Y. *Plant Cell* 23(5), 653-661.

Mourrain, P., Beclin, C., Elmayan, T., Feuerbach, F., Godon, C., Morel, J. -B., Jouette, D., Lacombe, A. -M., Nikic, S., Picault, N., Remoue, K., Sanial, M., Vo, T. -A., and Vaucheret, H. (2000). Arabidopsis SGS2 and SGS3 genes are required for posttranscriptional gene silencing and natural virus resistance. *Cell* 101, 533-542.

Niman, H. et al., (1983) Generation of protein-reactive antibodies by short peptides is an event of high frequency: Implications for the structural basis of immune recognition. *PNAS,* 80, 4949-4953.

Palauqui, J. -C., Elmayan, T., Pollien, J. -M., and Vaucheret, H. (1997). Systemic acquired silencing: transgene-specific post-transcriptional silencing is transmitted by grafting from silenced stocks to non-silenced scions. *EMBO J.* 16, 4738-4745.

Pruss, G., Ge, X., Shi, X. M., Carrington, J. C., and Vance, V. B. (1997). Plant viral synergism: the potyviral genome encodes a broad-range pathogenicity enhancer that trans-activates replication of heterologous viruses. *Plant Cell* 9, 859-868.

Ratcliff, F., Harrison, B. D., and Baulcombe, D. C. (1997). A similarity between viral defense and gene silencing in plants. *Science* 276, 1558-1560.

Ratcliff, F., MacFarlane, S., and Baulcombe, D. C. (1999). Gene silencing without DNA: RNA-mediated cross protection between viruses. *Plant Cell* 11, 1207-1215.

Rigaut G, Shevchenko A, Rutz B, Wilm M, Mann M, Seraphin B, (1999). A generic protein purification method for protein complex characterization and proteome exploration. *Nat Biotechnol.* Oct; 17(10):1030-32.

Romeis T, Piedras P, Jones J D, (2000). Resistance gene-dependent activation of a calcium-dependent protein kinase in the plant defense response. *Plant Cell.* May; 12(5):803-16.

Ruiz, F., Vassie, L., Klotz, K., Sperling, L., and Madeddu, L. (1998). Homology-dependent gene silencing in Paramecium. *Molecular Biology Of The Cell* 9, 931-943.

Ruiz, M. T., Voinnet, O., and Baulcombe, D. C. (1998). Initiation and maintenance of virus-induced gene silencing. *Plant Cell* 10, 937-946.

Vaucheret, H., Beclin, C., Elmayan, T., Feuerbach, F., Godon, C., Morel, J. -B., Mourrain, P., Palauqui, J. -C., and Vernhettes, S. (1998). Transgene-induced gene silencing in plants. *Plant J.* 16, 651-659.

Verchot, J., Angell, S. M., and Baulcombe, D. C. (1998). In Vivo Translation of the Entire Triple Gene Block of Potato Virus X Requires Two Separate mRNAs. *J. Virol.* 72, 8316-8320.

Voinnet, O., and Baulcombe, D. C. (1997). Systemic signalling in gene silencing. *Nature* 389, 553.

Voinnet, O., Pinto, Y. M., and Baulcombe, D. C. (1999). Suppression of gene silencing: a general strategy used by diverse DNA and RNA viruses. *Proc. Natl. Acad. Sci. USA* 96, 14147-14152.

Voinnet, O., Vain, P., Angell, S., and Baulcombe, D. C. (1998). Systemic spread of sequence-specific transgene RNA degradation is initiated by localised introduction of ectopic promoterless DNA. *Cell* 95, 177-187.

Whitham, S. A., Yamamoto, M. L., and Carrington, J. C. (1999). Selectable viruses and altered susceptibility mutants in Arabidopsis thaliana. *Proc. Natl. Acad. Sci. USA* 96, 772-777.

Zamore, P. D., Tuschl, T., Sharp, P. A., and Bartel, D. P. (2000). RNAi: Double-stranded RNA directs the ATP-dependent cleavage of mRNA at 21 to 23 nucleotide intervals. *Cell* 101, 25-33.

The invention claimed is:

1. A method of achieving enhanced expression from a target nucleotide sequence in a plant cell comprising,
   a) introducing a transient expression vector comprising said target nucleotide sequence into said plant cell for transient expression, wherein said vector is not a viral vector;
   b) introducing a non-naturally occurring nucleic acid encoding a post transcriptional gene silencing (PTGS) suppressor simultaneously with, prior to, or after introducing said target nucleic acid of step a), wherein said target nucleotide sequence is operably linked to a promoter and optionally comprises an origin of replication, wherein the PTGS suppressor enhances transient expression of the target nucleotide sequence relative to transient expression in the absence of the PTGS suppressor.

2. A method as claimed in claim 1 wherein the suppressor protein is of viral origin.

3. A method as claimed in claim 1 wherein the construct comprises
   (a) border sequences which permit the transfer of a desired nucleotide sequence into a plant cell genome; and
   (b) a desired nucleotide sequence which comprises an expression cassette including the target nucleotide sequence operably linked to a promoter.

4. A method as claimed claim 3 wherein the cell is a somatic cell present in a tissue of the plant.

5. A method as claimed in claim 4 wherein the construct is simultaneously introduced into a plurality of cells in the tissue.

6. A method as claimed in claim 5 wherein the suppressor protein is introduced into the cell by expression from a nucleic acid comprising a nucleotide sequence encoding the suppressor protein.

7. A method as claimed in claim 6 wherein a first target nucleic acid comprising the target nucleotide sequence is used with a second nucleic acid encoding the suppressor protein.

8. A method as claimed in claim 7, for achieving enhanced transient expression of a target nucleotide sequence in a plant, which method comprises the steps of introducing into a tissue of a plant a first nucleic acid comprising the target nucleotide sequence and a second nucleic acid encoding a PTGS suppressor protein, wherein the first and second nucleic acids are comprised within a single binary Agrobacterium vector construct and are expressed transiently, or the first and second nucleic acid sequences are comprised within a first binary vector and a second binary vector construct respectively.

9. A method for generating a target protein, which method comprises the steps of:
   (i) introducing into a tissue of a plant a first nucleic acid comprising a target nucleotide sequence and a second nucleic acid encoding a heterologous PTGS suppressor protein, said first and second nucleic acids being operably linked to at least one promoter, wherein the first and second nucleic acids are not present on a viral vector or vectors and at least said first nucleic acid is expressed transiently,
(ii) causing or permitting expression from the nucleic acids, over a period of time, of the suppressor and the target protein, wherein the suppressor inhibits degradation of the mRNA encoding the target protein,
(iii) harvesting the tissue in which the target protein has been expressed,
(iv) optionally isolating the target protein from the plant.

10. A method as claimed in claim 7 wherein the first nucleic acid comprises two or more target nucleotide sequences.

11. A method as claimed in claim 7 wherein each nucleic acid is present in a separate binary vector construct, which vectors are co-introduced into the plant.

12. A method as claimed in claim 7 wherein the nucleic acids are present in single binary vector construct.

13. A method as claimed in claim 9, wherein the period of time is selected from a time period of between about 3 to 15 days, about 3 to 10, and between about 4 to 7 days.

14. A method as claimed in claim 1 wherein the suppressor protein is selected from the group consisting of: potato virus X (pvx) p25 protein, African cassava mosaic virus (acmv) AC2 protein, rice yellow mottle virus (rymv) P1 protein, tomato bushy stunt virus (tbsv) 19K protein, rgs CAM or a variant of any one of these which shares at least about 95% sequence identity therewith.

15. The method as claimed in claim 1 wherein the construct is an agrobacterium vector.

16. The method as claimed in claim 11 or 12, wherein said nucleic acids are introduced into said cell in an agrobacterium vector.

17. A method of achieving enhanced expression from a target nucleotide sequence in a plant cell comprising,
a) introducing a transient expression vector comprising said target nucleotide sequence operably linked to a promoter into said plant cell for transient expression, wherein said vector is not a viral vector
b) introducing a non-naturally occurring nucleic acid encoding a post transcriptional gene silencing (PTGS) suppressor simultaneously with, prior to, or after introducing said target nucleic acid of step a), wherein said target nucleotide sequence is operably linked to a promoter and optionally comprises an origin of replication, wherein the PTGS suppressor enhances transient expression of the target nucleotide sequence relative to transient expression in the absence of the PTGS suppressor.

18. The method of claim 17, wherein said construct is an agrobacterium vector.

19. The method of claim 17, further comprising step c) isolating protein produced by an expression of said target nucleotide sequence.

* * * * *

SEQUENCE LISTING

<160> NUMBER OF SEQ ID NOS: 10

<210> SEQ ID NO 1
<211> LENGTH: 1133
<212> TYPE: DNA
<213> ORGANISM: Artificial
<220> FEATURE:
<223> OTHER INFORMATION: cDNA corresponding to a fragment of tobacco
      CDPK

<400> SEQUENCE: 1

| | | | | | |
|---|---|---|---|---|---|
| atggggaaca | cttgtgtagg | accaagcatt | tctaaaaatg | ggatctttca | atcagtttca | 60 |
| gcagcaatgt | ggcgatcccg | gtcgcccgat | gacactgctt | ccaccactaa | tggtgaaagt | 120 |
| gctagaattg | aaacaccaat | ttctgttaaa | gaacctgatt | cacctttgcc | agttcaagag | 180 |
| ccaccagaac | aaatgacaat | gcctaagtca | gaaaagaaag | aagaagaaaa | agaacaacca | 240 |
| aaaaagccca | aaaagcctgc | tgaaatgaag | agggtgtcaa | gtgctggcct | taggacagat | 300 |
| tctgtgttac | aaaagaaaac | tggaaactta | aaggagtttt | tcagtatagg | aaagaaatta | 360 |
| ggacaaggtc | aatttggaac | tacatttaaa | tgtgtcgaaa | aggcaacagg | aaggaatat | 420 |
| gcttgcaaat | cgattgctaa | gaggaagttg | ttaacagatg | atgatgtgga | agatgttaga | 480 |
| agggaagtac | agataatgca | ccatttggca | ggacatcctc | atgttatatc | gataaaaggt | 540 |
| gcttatgagg | atgctgtagc | tgttcatgta | gttatggagt | tttgtgctgg | gggtgagctt | 600 |
| ttcgatagga | ttattcaacg | ggggcactat | acagaaagaa | aagcagctga | gcttactagg | 660 |
| actattgttg | gagttgtaga | agcttgtcat | tctcttggtg | tcatgcatcg | tgatcttaag | 720 |
| cctgaaaatt | ttctctttgt | tgatcagaag | gaggattcac | ttctcaaagc | aattgacttt | 780 |
| gggttatcga | tattcttcaa | accaggcgac | agatttactg | atgttgttgg | cagtccatat | 840 |
| tatgttgcac | cagaagttct | ccgaaaacgt | tatggtcctg | aagctgatgt | ttggagtgct | 900 |
| ggtgtaatta | tctacatctt | attaagtgga | gtacctcctt | tctgggctga | aaatgagcaa | 960 |
| ggaatatttg | aacaagtcct | gcacggtgat | cttgacttca | cgtcagaccc | atggccaagt | 1020 |
| atttcagaag | atgcaaaaga | cttgatgagg | agaatgctcg | ttcgagatcc | gagaagacgt | 1080 |
| ttaactgcac | atgaagtttt | atgccatcct | tgggtacaag | ttgatggtgt | tga | 1133 |

<210> SEQ ID NO 2
<211> LENGTH: 1287
<212> TYPE: DNA
<213> ORGANISM: Artificial
<220> FEATURE:
<223> OTHER INFORMATION: GFP-RdRp fusion cDNA

<400> SEQUENCE: 2

| | | | | | |
|---|---|---|---|---|---|
| atgagtaaag | gagaagaact | tttcactgga | gttgtcccaa | ttcttgttga | attagatggt | 60 |
| gatgttaatg | ggcacaaatt | ttctgtcagt | ggagagggtg | aaggtgatgc | aacatacgga | 120 |
| aaacttaccc | ttaaatttat | ttgcactact | ggaaaactac | ctgttccatg | gccaacactt | 180 |
| gtcactactt | tctcttatgg | tgttcaatgc | ttttcaagat | acccagatca | tatgaagcgg | 240 |
| cacgacttct | tcaagagcgc | catgcctgag | ggatacgtgc | aggagaggac | catcttcttc | 300 |
| aaggacgacg | ggaactacaa | gacacgtgct | gaagtcaagt | ttgagggaga | caccctcgtc | 360 |
| aacaggatcg | agcttaaggg | aatcgatttc | aaggaggacg | gaaacatcct | cggccacaag | 420 |
| ttggaataca | actacaactc | ccacaacgta | tacatcatgg | cagacaaaca | aaagaatgga | 480 |
| atcaaagtta | acttcaaaat | tagacacaac | attgaagatg | gaagcgttca | actagcagac | 540 |

```
cattatcaac aaaatactcc aattggcgat ggccctgtcc ttttaccaga caaccattac    600
ctgtccacac aatctgccct ttcgaaagat cccaacgaaa agagagacca catggtcctt    660
cttgagtttg taacagctgc tgggattaca catggcatgg atgaactata caaatatgaa    720
gtgcaccatc aaggaaatga catggccaag gtgcgcgagg tttaccaatc tttacagact    780
ccaccacaaa aactctcatc aagatgaggc ttatagaaa cattcgcccc atcatggaaa     840
aacacaaact agctaaccct tacgctcaaa cggttgaagc ggctaatgat ctagaggggt    900
tcggcatagc caccaatccc tatagcattg aattcataca catgcagccg ctaagaccat    960
agagaataaa cttctagagg tgcttggttc catcctacca caagaacctg ttacatttat    1020
gtttcttaaa cccagaaagc taaactacat gagaagaaac ccgcggatca aggacatttt    1080
ccaaaatgtt gccattgacc aagagacgta gccaggtacc ccaaggaaac aataattgac    1140
aaactcacag agatcacaac ggaaacagca tacattagtg acactctgca cttcttggat    1200
ccgagctaca tagtggagac attccaaaac tgcccaaaat tgcaaacatt gtatgcgact    1260
tagttctccc cgttgaggca gcctaac                                       1287

<210> SEQ ID NO 3
<211> LENGTH: 17
<212> TYPE: DNA
<213> ORGANISM: Artificial
<220> FEATURE:
<223> OTHER INFORMATION: Primer

<400> SEQUENCE: 3
catcccgtgt cagtctg                                                  17

<210> SEQ ID NO 4
<211> LENGTH: 20
<212> TYPE: DNA
<213> ORGANISM: Artificial
<220> FEATURE:
<223> OTHER INFORMATION: Primer

<400> SEQUENCE: 4
atcacacggt tgtaaggttc                                               20

<210> SEQ ID NO 5
<211> LENGTH: 19
<212> TYPE: DNA
<213> ORGANISM: Artificial
<220> FEATURE:
<223> OTHER INFORMATION: Primer

<400> SEQUENCE: 5
atgactcggt tggaagttc                                                19

<210> SEQ ID NO 6
<211> LENGTH: 20
<212> TYPE: DNA
<213> ORGANISM: Artificial
<220> FEATURE:
<223> OTHER INFORMATION: Primer

<400> SEQUENCE: 6
gtagttgagg tagttgaccc                                               20

<210> SEQ ID NO 7
<211> LENGTH: 26
<212> TYPE: DNA
<213> ORGANISM: Artificial
```

```
<220> FEATURE:
<223> OTHER INFORMATION: Primer

<400> SEQUENCE: 7
gcacagattt tcctaggcac gttatc                                  26

<210> SEQ ID NO 8
<211> LENGTH: 26
<212> TYPE: DNA
<213> ORGANISM: Artificial
<220> FEATURE:
<223> OTHER INFORMATION: Primer

<400> SEQUENCE: 8
gaaagaaatt gggccggctc ttgaac                                  26

<210> SEQ ID NO 9
<211> LENGTH: 30
<212> TYPE: DNA
<213> ORGANISM: Artificial
<220> FEATURE:
<223> OTHER INFORMATION: Primer

<400> SEQUENCE: 9
cagaaaccgg ccgctagcgg gccattgccg                              30

<210> SEQ ID NO 10
<211> LENGTH: 23
<212> TYPE: DNA
<213> ORGANISM: Artificial
<220> FEATURE:
<223> OTHER INFORMATION: Primer

<400> SEQUENCE: 10
tgtactgctt gagatttaca gct                                     23
```